United States Patent [19]

Pawloski

[11] 4,451,653
[45] May 29, 1984

[54] HETEROCYCLIC SUBSTITUTED TRIAZOLYL PHOSPHOROUS COMPOUNDS

[75] Inventor: Chester E. Pawloski, Bay City, Mich.

[73] Assignee: The Dow Chemical Company, Midland, Mich.

[21] Appl. No.: 440,934

[22] Filed: Nov. 12, 1982

Related U.S. Application Data

[60] Division of Ser. No. 260,527, May 4, 1981, Pat. No. 4,400,516, which is a continuation-in-part of Ser. No. 951,923, Oct. 13, 1978, abandoned.

[51] Int. Cl.³ .................. C07D 237/30; C07D 241/10
[52] U.S. Cl. .................................... 544/238; 544/405; 544/407; 424/200
[58] Field of Search ............... 544/232, 238, 407, 405; 424/200

[56] References Cited

U.S. PATENT DOCUMENTS

| | | | |
|---|---|---|---|
| 3,686,200 | 8/1972 | Schrader et al. | 260/308 R |
| 3,689,500 | 9/1972 | Böhner et al. | 260/308 R |
| 3,867,396 | 2/1975 | Dawes et al. | 260/308 R |
| 3,867,397 | 2/1975 | Böhner et al. | 260/308 R |
| 3,867,398 | 2/1975 | Böhner et al. | 260/308 R |
| 3,879,412 | 4/1975 | Dawes et al. | 260/308 R |
| 3,956,306 | 5/1976 | Dawes et al. | 260/308 R |
| 3,992,399 | 11/1976 | Böhner et al. | 260/308 R |
| 4,035,487 | 7/1977 | Boehner et al. | 260/208 R |
| 4,357,328 | 11/1982 | Pawloski | 424/200 |
| 4,400,156 | 8/1983 | Pawloski | 546/276 |

Primary Examiner—Nicholas S. Rizzo
Attorney, Agent, or Firm—S. Preston Jones; Ronald G. Brookens

[57] ABSTRACT

Compounds are prepared which correspond to the formulae

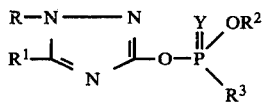

wherein R represents a nitrogen containing heterocyclic radical corresponding to one of the formulae

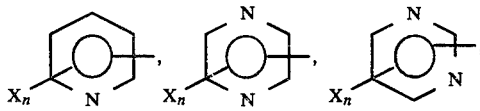

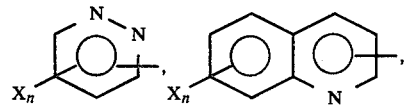

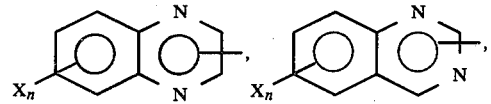

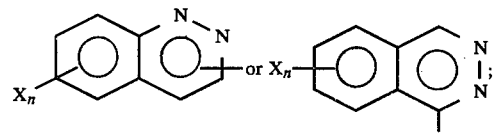

each X independently represents chloro, fluoro, bromo, nitro, alkyl of 1 to 4 carbon atoms, amino, mono- or dialkylamino wherein each alkyl group independently contains from 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, cyano, trifluoromethyl, trichloromethyl, phenoxy or substituted phenoxy of the formula

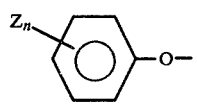

wherein each Z independently represents chloro, fluoro, bromo, nitro, cyano, alkoxy of 1 to 4 carbon atoms or alkylthio of 1 to 4 carbon atoms, with the proviso that when either n is 2 or 3, all X groups are sterically compatible with each other and all Z groups are sterically compatible with each other; Y represents oxygen or sulfur; each n can independently represent an integer of from 0 to 3, inclusive; R¹ represents hydrogen, chloro, fluoro, bromo, alkyl of 1 to 4 carbon atoms, cycloalkyl of 3–6 carbon atoms, phenyl, phenylthio, alkoxy of 1 to 4 carbon atoms, alkylthio of 1 to 4 carbon atoms, alkylsulfinyl of 1 to 4 carbon atoms, alkylsulfonyl of 1 to 4 carbon atoms, thiocyanato, trifluoromethyl, trichloromethyl, amino, mono- and dialkylamino wherein each alkyl group independently contains from 1 to 4 carbon atoms; R² represents methyl, ethyl, propyl or isobutyl and R³ represents methoxy, ethoxy, propoxy, ethyl, mono- or dialkylamino wherein each alkyl group independently contains from 1 to 4 carbon atoms, alkylthio of 1 to 4 carbon atoms or phenyl.

7 Claims, No Drawings

HETEROCYCLIC SUBSTITUTED TRIAZOLYL PHOSPHOROUS COMPOUNDS

CROSS-REFERENCE TO RELATED APPLICATION

This is a divisional of application Ser. No. 260,527, filed May 4, 1981, now U.S. Pat. No. 4,400,516, which is a continuation-in-part of application Ser. No. 951,923, filed Oct. 13, 1978, now abandoned.

SUMMARY OF THE INVENTION

The present invention is directed to heterocyclic substituted triazolyl phosphorous compounds corresponding to the formula

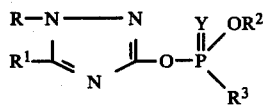

wherein R represents a nitrogen containing heterocyclic radical corresponding to one of the formulae

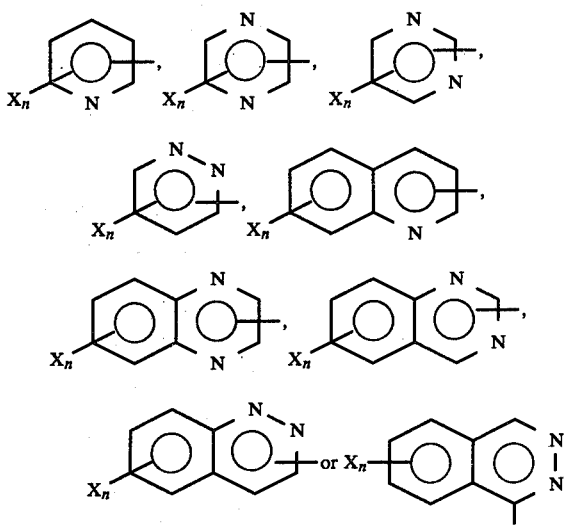

each X independently represents chloro, fluoro, bromo, nitro, alkyl of 1 to 4 carbon atoms, amino, mono- or dialkylamino wherein each alkyl group independently contains from 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, cyano, trifluoromethyl, trichloromethyl, phenoxy or substituted phenoxy of the formula

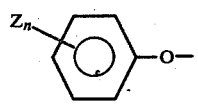

wherein each Z independently represents chloro, fluoro, bromo, nitro, cyano, alkoxy of 1 to 4 carbon atoms or alkylthio of 1 to 4 carbon atoms, with the proviso that when either n is 2 or 3, all X groups are sterically compatible with each other and all Z groups are sterically compatible with each other; Y represents oxygen or sulfur; each n can independently represent an integer of from 0 to 3, inclusive; $R^1$ represents hydrogen, chloro, fluoro, bromo, alkyl of 1 to 4 carbon atoms, cycloalkyl of 3–6 carbon atoms, phenyl, phenylthio, alkoxy of 1 to 4 carbon atoms, alkylthio of 1 to 4 carbon atoms, alkylsulfinyl of 1 to 4 carbon atoms, alkylsulfonyl of 1 to 4 carbon atoms, thiocyanato, trifluoromethyl, trichloromethyl, amino, mono- or dialkylamino wherein each alkyl group independently contains from 1 to 4 carbon atoms; $R^2$ represents methyl, ethyl, propyl or isobutyl and $R^3$ represents methoxy, ethoxy, propoxy, ethyl, mono- or dialkylamino wherein each alkyl group independently contains from 1 to 4 carbon atoms, alkylthio of 1 to 4 carbon atoms or phenyl.

In the present specification and claims, the term "sterically compatible" is employed to designate X and Z substituent groups which are not affected by steric hindrance as defined in "The Condensed Chemical Dictionary", 7th edition, Reinhold Publishing Co. N.Y., page 893 (1966) which definition is as follows:

"steric hindrance. A characteristic of molecular structure in which the molecules have a spatial arrangement of their atoms such that a given reaction with another molecule is prevented or rewarded in rate."

Steric hindrance may be further defined as compounds having substituents whose physical bulk does not require confinement within volumes insufficient for the exercise of their normal behavior as discussed in "Organic Chemistry" of D. J. Cram and G. Hammon, 2nd edition, McGraw-Hill Book Company, N.Y., page 215 (1964).

In the present specification and claims, the symbol "φ" is employed to designate phenyl or substituted phenyl.

The present invention is also directed to novel heterocyclic substituted triazol-3-ol compounds employed as starting materials in the preparation of the above heterocyclic substituted triazolyl phosphorous compounds. The triazol-3-ol compounds correspond to the formula

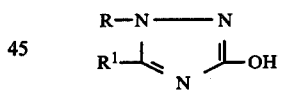

wherein R and $R^1$ are as hereinbefore set forth.

The triazolyl phosphorous compounds of the present invention possess excellent insecticidal properties and are very useful for the control of insects and for the protection of plants and stored goods from destruction by insects.

The phosphorous compounds of the present invention are crystalline solids or liquids which are sparingly soluble in water and which are soluble in most organic solvents.

A preferred group of phosphorous compounds are those wherein R is a heterocyclic radical corresponding to one of the formula

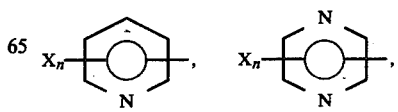

-continued

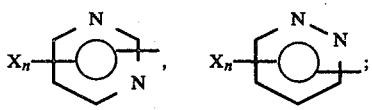

and X, n, Y, R$^1$, R$^2$, and R$^3$ are as hereinabove set forth.

Under this above group, an especially preferred group of compounds are those wherein R is

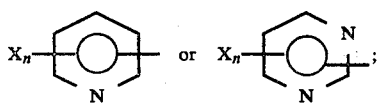

R$^2$ is C$_1$ or C$_2$ alkyl; R$^3$ is C$_1$ or C$_2$ alkoxy; X is chloro, fluoro, bromo or phenoxy; n is 0 or 1; Y is sulfur and R$^1$ is hydrogen, C$_1$ to C$_3$ alkyl, C$_1$ to C$_2$ alkoxy or C$_1$ to C$_2$ dialkylamino.

The triazolyl phosphorous compounds of the present invention can be prepared by the reaction of an appropriate substituted 3-hydroxy- or an alkali metal salt thereof which corresponds to the formula

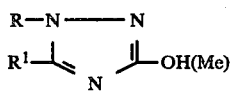

with a phosphoric acid halide corresponding to the formula

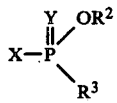

in the presence of an acid binding agent and a solvent. In the above formulae, R, R$^1$, R$^2$, R$^3$ and Y are as hereinbefore defined; Me represents sodium potassium, lithium or cesium and X represents chloro or bromo.

In carrying out this reaction, the 3-hydroxytriazole reactant or the alkali metal salt thereof; in a solvent, is mixed with the phosphoric acid halide and the mixture heated at a temperature of from about 20° C. up to the boiling point of the specific solvent employed. The reaction can be carried out if desired in the presence of a catalyst. The reaction is usually complete in from about 0.1 to about 24 hours.

The reaction consumes the reactants in stoichiometric proportions, i.e. one equivalent of the 3-hydroxytriazole reactant per equivalent of the phosphoric acid halide and for the most part, these amounts can be employed. It should be noted however, that the actual amount of the reactants to be employed is not critical as some of the desired product is formed when employing any proportions.

The alkali metal salt of 3-hydroxytriazole reactant can be prepared by the reaction of molecular equivalent amounts of the 3-hydroxytriazole and an alkali metal hydroxide or carbonate in the presence of a solvent at temperatures of from about 20° C. up to the reflux temperature of the solvent employed for from about 10 minutes to about 4 hours. From a practical standpoint, the salt conversion is usually carried out in situ. In addition, it is preferred to employ the alkali metal salt since during the subsequent reaction with the phosphorous acid halide, an insoluble alkali metal halide by-product is formed rather than an acid and no acid binding agent is necessary. Additionally, the insoluble salt can be easily removed allowing for a more convenient product recovery.

Representative catalysts useful in carrying out this process include tertiary amines having a pKa of at least about 9.5 as taught in U.S. Pat. No. 3,928,370. Additional catalytic agents which can be employed include co-catalysts which are mixtures of quaternary ammonium as phosphonium salts and organic tertiary amines such as taught in U.S. Pat. Nos. 3,907,815, 3,917,621, 4,007,197 and 4,016,225.

The ammonium salts are currently preferred over the phosphonium salts due to cost and commercial availability. The most preferred catalysts are benzyltrimethyl- , benzyltriethyl- tetra-n-butyl and tri-n-butylmethyl ammonium salts.

Examples of suitable tertiary amines include aliphatic trihydrocarbyl amines (e.g. trimethylamine, ethyldimethylamine, butyldimethylamine, N,N,N',N'-tetramethylethylenediamine, and the like); aliphatic heterocyclic amines (e.g. 1,4-diazabicyclo[2.2.2]octane, 1-azabicyclo[2.2.2]octane, 1-methyl-2-imidazoline, 1-methylpyrrolidine, and the like); mixed aliphatic-/aromatic amines (e.g. 4-dimethylaminopyridine, 4-(N-pyrrolidion)pyridine phenyldimethylamine, and the like; and other like organic, sterically unhindered, nucleophilic, tertiary amines.

Examples of suitable diazoles include imidazole, 1-methylimidazole, 1-ethylimidazole, 1-propylimidazole, 1-hexylimidazole pyrazole, 1-methylpyrazole, 1-ethylpyrazole, 1-butylpyrazole, 1-amylpyrazole and 1-hexylpyrazole, and the like.

Other catalysts include a heavy metal or heavy metal salt such as, for example, metallic copper or mercuric chloride.

If a catalyst is employed, it can be added at any stage of the process. In order to achieve the best yield, it is preferred that the catalyst be added at the beginning of the reaction. If, however, the catalyst is a tertiary amine, it is preferred that it be added just prior to the addition of the phosphorous acid chloride.

Suitable acid-binding agents are, for example, organic amines such as triethylamine, dimethylaniline, pyridine, inorganic bases such as the hydroxides and carbonates of alkali metals and alkaline earth metals, such as sodium, potassium, calcium, or lithium. These agents are employed in from about an equimolar amount up to about a 10 percent excess based on the triazole reactant.

Suitable solvents which can be employed are all the usual organic liquids which are insert under the reaction conditions, for example, acetone, methylethyl ketone, acetonitrile, ethyl acetate, butyl acetate, tetrahydrofuran, dioxane, methylene chloride, carbon tetrachloride, benzene, chlorobenzene, polychlorobenzenes, bromobenzene, dimethylformamide, xylene and the like.

DESCRIPTION OF SOME PREFERRED EMBODIMENTS

In order that the present invention may be more fully understood, the following examples are given primarily by way of illustration and should not be construed as limitations upon the overall scope of the present invention.

EXAMPLE I

O,O-Diethyl
O-(1-(6-fluoro-2-pyridinyl)-1H-1,2,4-triazol-3-yl)
phosphorothioate

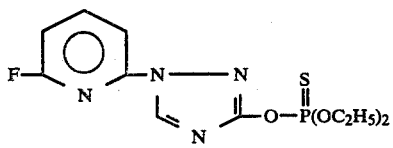

Into a 500 milliliter (ml) flask equipped with a stirrer and a reflux condenser were placed 9 grams (g) (0.05 mole (m)) of 1-(6-fluoro-2-pyridinyl)-1H-1,2,4-triazol-3-ol, 7 g (0.05 m) of potassium carbonate, 1 g of mercuric chloride and 200 mls of acetonitrile. This mixture was stirred and heated to 70° C. for two hours and allowed to cool. To this mixture was added 9 g (0.05 m) of O,O-diethyl phosphorochloridothioate and the mixture heated to 70° C. for 16 hours and allowed to cool. The insolubles were removed by filtration and the solvent was removed from the filtrate by distillation at 60° C. under reduced pressure. The oil which remained was taken up in 300 mls of methylene chloride, washed twice with 150 ml portions of water, separated, dried over anhydrous sodium sulfate, filtered and the methylene chloride was removed by distillation leaving 14 grams (84 percent of theoretical) of the desired O,O-diethyl O-(1-(6-fluoro-2-pyridinyl)-1H-1,2,4-triazol-3-yl) phosphorothioate. The product was a white solid melting at 80°–82° C. Upon analysis, the compound was found to have carbon, hydrogen and nitrogen contents of 39.33, 4.19 and 16.73 percent, respectively, as compared with the theoretical contents of 39.76, 4.25 and 16.86 percent, respectively, calculated for the above named compound. (Compound 1).

EXAMPLE II

O,O-Diethyl
O-(1-(6-fluoro-2-pyridinyl)-5-methyl-1H-1,2,4-triazol-3-yl) phosphorothioate

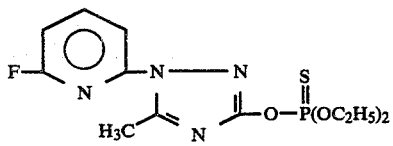

A 3-neck, 500-ml flask was charged with 9 g (0.046 m) of 1-(6-fluoro-2-pyridinyl)-5-methyl-1H-1,2,-4-triazol-3-ol, 6.6 grams (0.048 m) of dry potassium carbonate and 150 ml of acetonitrile. The mixture was refluxed for 2 hours and then cooled to 25° C. To this mixture was added 8.67 g (0.046 m) of O,O-diethyl phosphorochloridothioate and the mixture was heated to 75° C. for 3½ hours. The solid material which formed was removed by filtration and the acetonitrile was removed by evaporation under reduced pressure. The solid residue which remained was taken up in ethyl ether, washed with 2 percent sodium hydroxide and dried over sodium sulfate. The desired O,O-diethyl O-(1-(6-fluoro-2-pyridinyl)-5-methyl-1H-1,2,4-triazol-3-yl) phosphorothioate was crystallized from a 50:50 mixture of ethyl ether and hexane in a yield of 12.9 g (85 percent of theoretical). The product melted at 68°–70° C. and upon analysis was found to have carbon, hydrogen and nitrogen contents of 41.54, 4.66 and 16.05 percent, respectively, as compared to the theoretical contents of 41.62, 4.66 and 16.18 percent, respectively, as calculated for the above named compound. (Compound 2).

EXAMPLE III

O,O-Diethyl
O-(1-(6-chloro-2-pyrazinyl)-1H-1,2,4-triazol-3-yl)
phosphorothioate

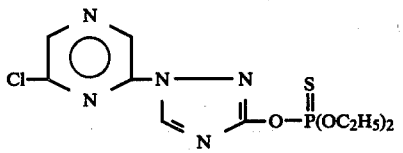

Into a 500-ml flask were placed 7 g (0.035 m) of 1-(6-chloro-2-pyrazinyl)-1H-1,2,4-triazol-3-ol, 5 g (0.035 m) of potassium carbonate, 0.5 g of mercuric chloride and 150 mls of acetonitrile. The mixture was stirred and heated to 70° C. for one hour and then allowed to cool to room temperature. To this mixture was added 6.5 g (0.035 m) of O,O-diethyl phosphorochloridothioate and the mixture stirred and heated to 65° C. for 13 hours. The reaction mixture was cooled and filtered to remove the insoluble by-product and the solvent then removed by evaporation at 50° C. under reduced pressure. The oil product which remained was taken up in 250 mls of methylene chloride and then washed twice with 200 mls of water, separated, dried over anhydrous sodium sulfate, filtered and the solvent removed by evaporation under reduced pressure. The crude O,O-diethyl-O-(1-(6-chloro-2-pyrazinyl)-1H-1,2,4-triazol-3-yl) phosphorothioate product thus obtained was purified by recrystallization from hexane. The purified product was recovered in a yield of 5.9 grams (49 percent of theoretical) and melted at 77°–78° C. Upon analysis, the compound was found to have carbon, hydrogen and nitrogen contents of 34.27, 3.84 and 20.26 percent, respectively, as compared with the theoretical contents of 34.34, 3.75 and 20.03 percent, respectively, calculated for the above named compound. (Compound 3).

EXAMPLE IV

O,O-Diethyl O-(1-(3-quinolinyl)-1H-1,2,4-triazol-3-yl) phosphorothioate

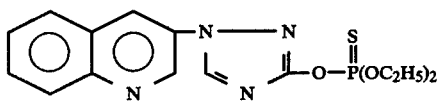

Into a 500-ml flask were placed 5.3 g (0.025 m) of 1-(3-quinolinyl)-1H-1,2,4-triazol-3-ol, 4 g (0.025 m) of potassium carbonate, 0.2 g of mercuric chloride and 150 ml of acetonitrile. The mixture was stirred and refluxed for ~2 hours and then allowed to cool to room temperature. To this mixture was added 4.7 grams (0.025 m) of O,O-diethyl phosphorochloridothioate and the mixture heated to 75° C. for 20 hours and allowed to cool to room temperature. The mixture was filtered and the solvent removed by evaporation under reduced pressure. The oil which remained as a residue was taken up in 300 mls of methylene chloride and washed twice with 250 ml portions of water. The oil was separated, dried over anhydrous sodium sulfate and distilled to yield 4 grams of oil. The oil was admixed with 5 ml of methanol and 100 mls of n-hexane. The solid 0,0-diethyl 0-(1-3-quinolinyl)-1H-1,2,4-triazol-3-yl) phosphorothioate which precipitated was recovered in a yield of 2.1 grams (23 percent of theoretical) and melted at 95°-v° C. Upon analysis, the compound was found to have carbon, hydrogen and nitrogen contents of 49.49, 4.94 and 15.43 percent, respectively, as compared with the theoretical contents of 49.44, 4.70 and 15.38 percent, respectively, calculated for the above named compound. (Compound 4).

EXAMPLE V
0,0-Diethyl 0-(1-(6-chloro-3-pyridazinyl)-1H-1,2,4-triazol-3-yl) phosphorothioate

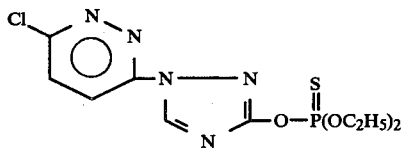

Into a 500-ml three-necked flask equipped with a stirrer and reflux condenser were placed 6.5 g (0.033 m) of 1-(6-chloro-3-pyridazinyl)-1H-1,2,4-triazol-3-ol, 5 g (0.033 m) of potassium carbonate, 0.5 g of mercuric-chloride and 100 mls of acetonitrile. The mixture was stirred and heated to 70° C. for one hour and cooled. To this mixture was added 5.6 g (0.03 m) of 0,0-diethyl phosphorochloridothioate and the mixture was heated at 60° C. for 6 hours and cooled. The insolubles which formed were removed by filtration and the solvent was then removed by evaporation at 60° C. under reduced pressure. The oil which remained was taken up in 250 mls of methylene chloride sequentially washed with 200 mls of water, 200 mls of a 2 percent sodium hydroxide solution and 200 mls of water and then separated, dried over anhydrous sodium sulfate, filtered and the solvent removed by evaporation under reduced pressure leaving 4 grams of an oil product. The 0,0-diethyl 0-(1-(6-chloro-3-pyridazinyl)-1H-1,2,4-triazol-3-yl) phosphorothioate product was crystallized from warm hexane in a yield of 1.7 grams (15 percent of theoretical). The product melted at 46°-49° C. NMR (60MHz) (CDCl$_3$, δ): 9.00 (s,1H); 8.18 (d, J=10.0 1H); 7.00 (d, J=10.0 1H); 4.35 (d of q, J=10.5, 6.5, 4H); 1.43 (t w/fine coupling, J=6.5 6H). (Compound 5).

EXAMPLE VI
0,0-Dimethyl 0-(1-(2-pyridinyl)-1H-1,2,4-triazol-3-yl )phosphorothioate

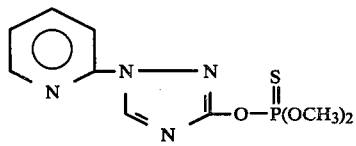

A mixture of 8.10 g (0.05 m) of 1-(2-pyridinyl)-1H-1,2,4-triazol-3-ol and 8.29 g (0.06 m) of powdered potassium carbonate in 150 ml of acetonitrile was vigorously stirred together for 2½ hours at 40°-50° C. To this mixture was successively added a solution of 0.29 g (0.0024 m (5 mole percent))of 4-dimethylaminopyridine in 25 ml of acetonitrile followed by a solution of 7.94 g (0.048 m) of 0,0-dimethyl phosphorochloridothioate in 25 ml of acetonitrile. After a 2 hour period, the reaction was complete and the reaction mixture was filtered and evaporated to dryness. The oil which remained as a residue was triturated with hexane and solidification occurred. The solid, crude 0,0-dimethyl 0-(1-(2-pyridinyl)-1H-1,2,4-triazol-3-yl) phosphorothioate product was recovered in a yield of 11.3 g (82 percent of theoretical) and melted at 88°-91° C. The product after recrystallization from methyl cyclohexane melted at 95°-96° C. Upon analysis, the product was found to have carbon, hydrogen and nitrogen contents of 37.68, 3.91 and 19.51 percent, respectively, as compared with the theoretical contents of 37.76, 3.87 and 19.58 percent, respectively, as calculated for the named compound. (Compound 6).

By following the procedures as set forth in the above examples, and employing the appropriate reactants, the following compounds in Table I are prepared.

TABLE I

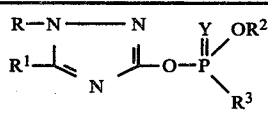

| Compound No. | R | R$^1$ | R$^2$ | R$^3$ | Y | Molecular Weight | Physical Data |
|---|---|---|---|---|---|---|---|
| 7 | Cl-(pyridine) | —H | —C$_2$H$_5$ | —OC$_2$H$_5$ | S | 348.75 | MP. 69°-70° C. |
| 8 | Cl,Cl,Cl-(pyridine) | —H | —C$_2$H$_5$ | —OC$_2$H$_5$ | S | 417.64 | MP. 72°-76° C. |
| 9 | Cl-(pyridine) | —H | —C$_2$H$_5$ | —OC$_2$H$_5$ | S | 348.75 | MP. 89°-91° C. |

TABLE I-continued

R—N——N
R¹—C=N—O—P(=Y)(OR²)(R³)

| Compound No. | R | R¹ | R² | R³ | Y | Molecular Weight | Physical Data |
|---|---|---|---|---|---|---|---|
| 10 | 2-pyridyl | —CH₃ | —C₂H₅ | —OC₂H₅ | S | 328.33 | MP. 43°–45° C. |
| 11 | 6-methoxy-2-pyridyl (H₃CO-) | —H | —C₂H₅ | —OC₂H₅ | S | 344.33 | $n_D^{25} = 1.5458$ |
| 12 | 6-fluoro-2-pyridyl (F-) | —H | —C₂H₅ | —φ | S | 364.34 | MP. 78°–83° C. |
| 13 | 6-chloro-2-pyridyl (Cl-) | —H | —C₂H₅ | —φ | S | 380.79 | MP. 75°–78° C. |
| 14 | 4-(SC₄H₉)-2-pyridyl | —H | —C₂H₅ | —OC₂H₅ | O | 402.47 | |
| 15 | 5-nitro-2-pyridyl (O₂N-) | —H | —C₂H₅ | —OC₂H₅ | S | 359.30 | MP. 98°–100° C. |
| 16 | 5-nitro-2-pyridyl (O₂N-) | —SC₄H₉ | —CH₃ | —OCH₃ | S | 419.42 | |
| 17 | 4-cyano-2-pyridyl (CN-) | —CH₃ | —CH₃ | —OCH₃ | O | 309.22 | |
| 18 | 6-phenoxy-2-pyridyl (φ-O-) | —φ | —CH₃ | —OCH₃ | O | 438.38 | |
| 19 | 3,5-bis(CF₃)-2-pyridyl | —CF₃ | —CH₃ | —OCH₃ | S | 490.25 | |
| 20 | 6-(methylthio)-2-pyridyl (H₃CS-) | —H | —C₂H₅ | —OC₂H₅ | S | 360.40 | MP. 34°–36° C. |

TABLE I-continued $$\begin{array}{c} R-N\text{———}N \\ R^1\diagdown\phantom{xx}\diagup \\ =\phantom{xxx}\overset{\overset{\displaystyle Y}{\|}}{C}-O-\overset{\overset{\displaystyle Y}{\|}}{P}\diagup\overset{\displaystyle OR^2}{} \\ N\phantom{xxxxxxxx}R^3 \end{array}$$

| Compound No. | R | $R^1$ | $R^2$ | $R^3$ | Y | Molecular Weight | Physical Data |
|---|---|---|---|---|---|---|---|
| 21 | 3-CH₃, 2-SCH₃ pyridine | —H | —C₂H₅ | —OC₂H₅ | S | 374.42 | MP. 50°–53° C. |
| 22 | φ-O-pyridine | —N(CH₃)₂ | —C₂H₅ | —OC₂H₅ | O | 433.41 | |
| 23 | pyridine | —SCH₃ | —CH₃ | —SCH₃ | S | 348.40 | |
| 24 | pyridine | —S(O)CH₃ | —CH₃ | —OCH₃ | S | 348.34 | |
| 25 | pyridine | —S(O)₂—C₄H₉ | —CH₃ | —N(CH₃)₂ | S | 419.46 | |
| 26 | 2,6-(CH₃)₂ pyridine | —H | —C₂H₅ | —OC₂H₅ | S | 342.36 | |
| 27 | 2-SCH₃, 6-CH₃ pyridine | —H | —C₂H₅ | —OC₂H₅ | S | 374.42 | MP. 105°–109° C. |
| 28 | 2-Cl pyridine | —H | —C₂H₅ | —NHCH₃ | S | 333.74 | MP. 102°–105° C. |
| 29 | pyridine | —F | —C₂H₅ | —OC₂H₅ | O | 316.23 | |
| 30 | trichloropyrazine | —Cl | —CH₃ | —OCH₃ | S | 425.02 | |
| 31 | trichloropyrazine | —CH₃ | —C₂H₅ | —NHC₄H₉ | O | 337.30 | |

TABLE I-continued $$R-N-N$$
$$R^1-C(=N)-O-P(=Y)(OR^2)(R^3)$$

| Compound No. | R | R¹ | R² | R³ | Y | Molecular Weight | Physical Data |
|---|---|---|---|---|---|---|---|
| 32 | 3,5-difluoropyrazine | —OCH₃ | —CH₃ | —OC₃H₇ | S | 381.30 | |
| 33 | 3,5-dichloro-6-fluoropyridine | —Br | —CH₃ | —φ | S | 498.10 | |
| 34 | 2,4,6-trimethylpyridine | —C₄H₉ | —CH₃ | —OCH₃ | S | 370.41 | |
| 35 | pyridine | —Cl | —C₂H₅ | —OC₂H₅ | S | 348.75 | MP. 27°–28° C. |
| 36 | 3,6-dimethylpyridazine | —CH₃ | —CH₃ | —OCH₃ | O | 299.23 | |
| 37 | 4-methyl-6-(methylthio)pyrimidine | —N(C₄H₉)₂ | —CH₃ | —N(C₄H₉)₂ | S | 557.75 | |
| 38 | pyridine | —NH₂ | —C₃H₇ | —OC₃H₇ | S | 357.37 | |
| 39 | 6-(methylsulfonyl)pyridine | —F | —CH₃ | —OCH₃ | S | 382.33 | |
| 40 | 5-(butylsulfinyl)pyridine | —OC₄H₉ | —C₃H₇ | —NHC₃H₇ | O | 500.55 | |
| 41 | 6-cyanoquinoline | —F | —C₂H₅ | —N(C₂H₅)₂ | O | 418.36 | |
| 42 | 4-chloro-2-cyanopyridine | —CCl₃ | —C₃H₇ | —SC₃H₇ | S | 535.23 | |

TABLE I-continued

Structure:
$$R-N(R^1C=N-)-N=C(-)-O-P(=Y)(OR^2)(R^3)$$

| Compound No. | R | R¹ | R² | R³ | Y | Molecular Weight | Physical Data |
|---|---|---|---|---|---|---|---|
| 43 | 7-butoxy-5-fluoroquinazolin-2-yl | —H | —$C_2H_5$ | —$OC_2H_5$ | S | 455.45 | |
| 44 | 4-methyl-2-chloropyridin-6-yl | —H | —$C_2H_5$ | —$OC_2H_5$ | S | 348.75 | $n_D^{25}$ = 1.5549 |
| 45 | 2,6-dichloropyridin-3-yl | —H | —$C_2H_5$ | —$OC_2H_5$ | S | 383.26 | $n_D^{25}$ = 1.5644 |
| 46 | pyridin-2-yl | —H | —$C_2H_5$ | —$OC_2H_5$ | S | 314.31 | MP. 60°–63° C. |
| 47 | 6-chloropyridin-2-yl | —H | i-$C_4H_9$ | —$OC_2H_5$ | S | 376.80 | MP. 69°–71° C. |
| 48 | 5-chloropyridin-2-yl | —$CH_3$ | —$C_2H_5$ | —$OC_2H_5$ | S | 362.78 | MP. 40°–41° C. |
| 49 | quinolin-2-yl | —$NHC_4H_9$ | —$CH_3$ | —$NHCH_3$ | S | 406.45 | |
| 50 | phthalazin-1-yl | —$C_3H_5$ | —$CH_3$ | —φ | S | 423.43 | |
| 51 | quinazolin-2-yl | —$C_6H_{11}$ | —$CH_3$ | —φ | O | 449.45 | |
| 52 | cinnolin-3-yl | —$NHCH_3$ | —$C_2H_5$ | —$N(C_2H_5)_2$ | O | 405.40 | |
| 53 | quinoxalin-2-yl | —$SO_2CH_3$ | —$CH_3$ | —$SCH_3$ | S | 431.45 | |

TABLE I-continued
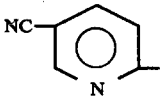
| Compound No. | R | R¹ | R² | R³ | Y | Molecular Weight | Physical Data |
|---|---|---|---|---|---|---|---|
| 54 | 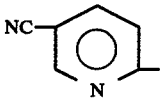 | —H | —C$_2$H$_5$ | —OC$_2$H$_5$ | S | 339.31 | MP. 116°–117° C. |
| 55 | 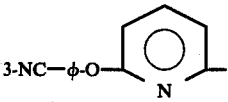 | —CH$_3$ | —C$_2$H$_5$ | —OC$_2$H$_5$ | S | 353.34 | MP. 92°–93° C. |
| 56 | 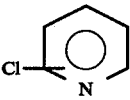 | —CH$_3$ | —C$_2$H$_5$ | —OC$_2$H$_5$ | S | 445.44 | |
| 57 | 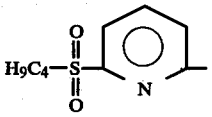 | —SC$_4$H$_9$ | —CH$_3$ | —OCH$_3$ | O | 392.80 | |
| 58 | 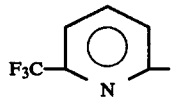 | —CH$_3$ | —CH$_3$ | —OCH$_3$ | S | 420.44 | |
| 59 | 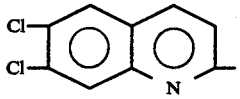 | —N(CH$_2$CH=CH$_2$)$_2$ | —C$_2$H$_5$ | —C$_2$H$_5$ | S | 463.44 | |
| 60 |  | —H | —C$_2$H$_5$ | —OC$_2$H$_5$ | S | 433.26 | |
| 61 | 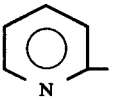 | —H | —C$_2$H$_5$ | —OC$_2$H$_5$ | O | 348.30 | |
| 62 | 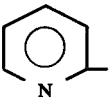 | —C$_2$H$_5$ | —C$_2$H$_5$ | —OC$_2$H$_5$ | S | 342.36 | MP. 38°–40° C. |
| 63 | 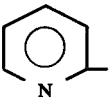 | —H | —C$_2$H$_5$ | —OC$_2$H$_5$ | S | 314.31 | MP. 24°–28° C. |
| 64 | 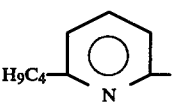 | —OC$_4$H$_9$ | —C$_2$H$_5$ | —SC$_4$H$_9$ | S | 486.64 | |

TABLE I-continued $$R-N-N$$
$$R^1 \underset{N}{\overset{\|}{\diagdown}} O-P\overset{Y}{\underset{R^3}{\overset{\|}{\diagdown}}} OR^2$$

| Compound No. | R | $R^1$ | $R^2$ | $R^3$ | Y | Molecular Weight | Physical Data |
|---|---|---|---|---|---|---|---|
| 65 | F$_3$C—pyridinyl | —H | —C$_2$H$_5$ | —OC$_2$H$_5$ | S | 382.30 | MP. 46°–48° C. |
| 66 | Br—pyrazinyl | —CCl$_3$ | —CH$_3$ | —SCH$_3$ | S | 499.57 | |
| 67 | pyrazinyl | —t-C$_4$H$_9$ | —CH$_3$ | —OCH$_3$ | O | 327.28 | |
| 68 | pyrazinyl | —SOC$_4$H$_9$ | —CH$_3$ | —OCH$_3$ | S | 391.41 | |
| 69 | Br—pyridinyl | —H | —C$_2$H$_5$ | —OC$_2$H$_5$ | S | 393.21 | MP. 60°–62° |
| 70 | quinolinyl | —H | —C$_2$H$_5$ | —OC$_2$H$_5$ | S | 364.37 | MP. 71°–72° C. |
| 71 | pyridinyl | —SC$_2$H$_5$ | —C$_2$H$_5$ | —OC$_2$H$_5$ | S | 374.40 | MP. 45°–48° C. |
| 72 | pyridinyl | OCH$_3$ | —C$_2$H$_5$ | —OC$_2$H$_5$ | S | 344.33 | $n_D^{25}$ = 1.5360 |
| 73 | Cl—pyridinyl | —H | —CH$_3$ | —OCH$_3$ | S | 320.70 | MP. 87°–88° C. |
| 74 | Cl—pyridinyl(CCl$_3$) | —H | —C$_2$H$_5$ | —OC$_2$H$_5$ | S | 466.05 | $n_d^{25}$ = 1.5494 |
| 75 | pyridinyl | —H | —C$_2$H$_5$ | —OC$_2$H$_5$ | O | 298.3 | MP. 40° C. |

TABLE I-continued

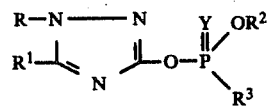

| Compound No. | R | R¹ | R² | R³ | Y | Molecular Weight | Physical Data |
|---|---|---|---|---|---|---|---|
| 76 | 2-pyridyl | —N(CH₃)₂ | —C₂H₅ | —OC₂H₅ | S | 357.30 | $n_D^{25} = 1.5365$ |
| 77 | 6-chloro-2-pyridyl | —CH₃ | —C₂H₅ | —OC₂H₅ | S | 362.7 | MP. 56°–59° C. |
| 78 | 2-pyridyl | —S—φ | —C₂H₅ | —OC₂H₅ | S | 422.32 | MP. 80°–82° C. |
| 79 | 6-chloro-2-pyridyl | —H | —C₂H₅ | —SC₃H₇ | S | 378.90 | $n_D^{25} = 1.5887$ |
| 80 | 2-pyridyl | —CH₃ | —C₂H₅ | —SC₃H₇ | S | 358.40 | $n_D^{25} = 1.5746$ |
| 81 | 2-pyridyl | —CH₃ | —C₃H₇ | —OC₃H₇ | S | 356.40 | $n_D^{25} = 1.5329$ |
| 82 | 2-pyridyl | —SCN | —C₂H₅ | —OC₂H₅ | S | 371.24 | MP. 99°–100° C. |
| 83 | 2-pyridyl | —CH₃ | —CH₃ | —OCH₃ | S | 300.30 | MP. 60°–61° C. |
| 84 | 2-pyridyl | —H | —C₂H₅ | —SC₃H₇ | S | 344.40 | $n_D^{25} = 1.5821$ |
| 85 | 2-pyridyl | —H | —C₃H₇ | —OC₃H₇ | S | 342.2 | $n_D^{25} = 1.5375$ |
| 86 | 2-pyridyl | —H | —C₂H₅ | —N(C₄H₉)₂ | S | 397.48 | |
| 87 | 6-methyl-2-pyridyl | —CH₃ | —C₂H₅ | —OC₂H₅ | S | 342.36 | MP. 49°–51° C. |

TABLE I-continued $$\begin{array}{c} R-N\!\!-\!\!-\!\!N \\ R^1\!\!\diagdown\!\!\diagup \quad \diagdown\!\!\diagup\!\!-\!\!O\!-\!\!\overset{Y}{\underset{R^3}{\overset{\|}{P}}}\!\!-\!\!OR^2 \\ N \end{array}$$

| Compound No. | R | $R^1$ | $R^2$ | $R^3$ | Y | Molecular Weight | Physical Data |
|---|---|---|---|---|---|---|---|
| 88 | 2-(F₃C)-pyridin-6-yl | —CH₃ | —C₂H₅ | —OC₂H₅ | S | 396.33 | MP. 67°–68° C. |
| 89 | 5-Br-pyrazin-2-yl | —H | —C₂H₅ | —OC₂H₅ | S | 394.18 | |
| 90 | 6-Br-pyridazin-3-yl | —CH₃ | —C₂H₅ | —OC₂H₅ | S | 408.21 | |
| 91 | 5-(H₃CS)-pyrazin-2-yl | —H | —C₂H₅ | —OC₂H₅ | S | 361.38 | |
| 92 | 6-(H₃CS)-pyridazin-3-yl | —CH₃ | —C₂H₅ | —OC₂H₅ | S | 375.41 | |
| 93 | 5-(H₃CO)-pyridin-2-yl | —CH₃ | —C₂H₅ | —OC₂H₅ | S | 359.19 | |
| 94 | 5-(H₃CS)-pyridin-2-yl | —CH₃ | —C₂H₅ | —OC₂H₅ | S | 375.41 | |
| 95 | 6-(H₃CS)-pyridin-2-yl | —CH₃ | —C₂H₅ | —OC₂H₅ | S | 374.42 | MP. 61°–63° C. |
| 96 | 6-(H₃CSO₂)-pyridin-2-yl | —H | —C₂H₅ | —OC₂H₅ | S | 392.39 | MP. 82°–85° C. |
| 97 | 6-(H₃CSO₂)-pyridin-2-yl | —CH₃ | —C₂H₅ | —OC₂H₅ | S | 406.42 | |
| 98 | 6-(H₃CO)-pyridin-2-yl | —CH₃ | —C₂H₅ | —OC₂H₅ | S | 358.36 | MP. 61.5°–63° C. |

TABLE I-continued $$R-N-N$$
$$R^1 \underset{N}{=} \overset{}{\underset{O-P}{\overset{Y}{\underset{R^3}{\parallel}}}} OR^2$$

| Compound No. | R | $R^1$ | $R^2$ | $R^3$ | Y | Molecular Weight | Physical Data |
|---|---|---|---|---|---|---|---|
| 99 | 6-methyl-2-methoxypyridin-3-yl ($H_3CO$-pyridine-$CH_3$) | —H | —$C_2H_5$ | —$OC_2H_5$ | S | 344.33 | MP. 58°–60° C. |
| 100 | 6-methyl-2-phenoxypyridin-3-yl (φ-O-pyridine-$CH_3$) | —H | —$C_2H_5$ | —$OC_2H_5$ | S | 406.40 | MP. 45°–47° C. |
| 101 | 6-methyl-2-phenoxypyridin-3-yl (φ-O-pyridine-$CH_3$) | —$CH_3$ | —$C_2H_5$ | —$OC_2H_5$ | S | 420.43 | $n_D^{25}$ = 1.5628 |
| 102 | 6-methyl-2-dimethylaminopyridin-3-yl (($CH_3$)$_2$N-pyridine-$CH_3$) | —H | —$C_2H_5$ | —$OC_2H_5$ | S | 357.37 | MP. 94°–96° C. |
| 103 | 6-methyl-2-(N-methyl-N-butyl)aminopyridin-3-yl | —$CH_3$ | —$C_2H_5$ | —$OC_2H_5$ | S | 413.48 | |
| 104 | 6-methyl-2-methylsulfonylpyridin-3-yl ($H_3C$-SO$_2$-pyridine) | —$CF_3$ | —$C_2H_5$ | —$OC_2H_5$ | S | 460.39 | |
| 105 | pyridinyl | —φ | —$C_2H_5$ | —$OC_2H_5$ | S | 390.40 | MP. 58°–59° C. |
| 106 | pyridinyl | —t-$C_4H_9$ | —$C_2H_5$ | —$OC_2H_5$ | S | 370.40 | |
| 107 | pyridinyl | —$C_3H_3$ | —$C_2H_5$ | —$OC_2H_5$ | S | 354.37 | |
| 108 | pyridinyl | —$NH_2$ | —$C_2H_5$ | —$OC_2H_5$ | S | 329.32 | MP. 129°–131° C. |
| 109 | pyridinyl | —N($CH_3$)$_2$ | —$C_2H_5$ | —$OC_2H_5$ | S | 357.37 | |

TABLE I-continued
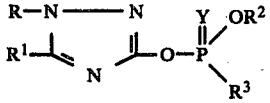
| Compound No. | R | R¹ | R² | R³ | Y | Molecular Weight | Physical Data |
|---|---|---|---|---|---|---|---|
| 110 | 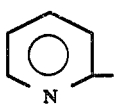 | —CCl₃ | —C₂H₅ | —OC₂H₅ | S | 431.67 | |
| 111 | 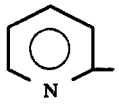 | —C₆H₁₁ | —C₂H₅ | —OC₂H₅ | S | 396.45 | |
| 112 | 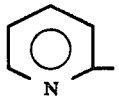 | —Br | —C₂H₅ | —OC₂H₅ | S | 393.21 | |
| 113 | 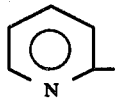 | —F | —C₂H₅ | —OC₂H₅ | S | 332.30 | |
| 114 | 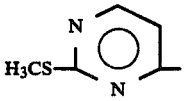 | —H | —CH₃ | —OCH₃ | S | 333.33 | MP. 88°–90° C. |
| 115 | 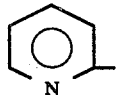 | —CH₃ | —CH₃ | —NH—i-C₃H₇ | S | 327.34 | |
| 116 | 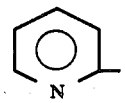 | —H | —CH₃ | —NH—i-C₃H₇ | S | 313.32 | |
| 117 | 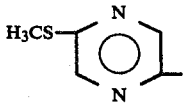 | —CH₃ | —C₂H₅ | —OC₂H₅ | S | 375.41 | |
| 118 |  | —CH₃ | —C₂H₅ | —OC₂H₅ | S | 363.76 | |
| 119 | 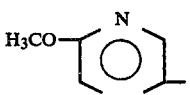 | —H | —C₂H₅ | —OC₂H₅ | S | 345.32 | |
| 120 | 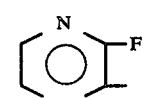 | —H | —C₂H₅ | —OC₂H₅ | S | 333.29 | |
| 121 | 3,5-(NO₂)₂—φ-O— 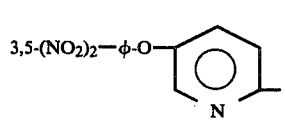 | —H | —C₂H₅ | —OC₂H₅ | S | 496.38 | |

TABLE I-continued

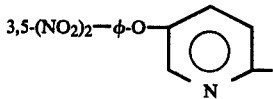

| Compound No. | R | R¹ | R² | R³ | Y | Molecular Weight | Physical Data |
|---|---|---|---|---|---|---|---|
| 122 | 3,5-(NO₂)₂—φ-O— (pyridyl) | —CH₃ | —C₂H₅ | —OC₂H₅ | S | 510.43 | |
| 123 | H₂N—(pyridyl) | —N(CH₃)C₄H₉ | —CH₃ | —N(CH₃)C₄H₉ | O | 425.47 | |
| 124 | H₂N—(pyridyl)—NH₂ | —N(C₄H₉)₂ | —C₃H₇ | —N(CH₃)C₂H₅ | O | 482.57 | |
| 125 | Cl—(pyridyl) | —CH₃ | —CH₃ | —OCH₃ | S | 335.71 | MP. 64.5°–66° C. |
| 126 | H₃CS—(pyridyl) | —CH₃ | —CH₃ | —OCH₃ | S | 347.43 | MP. 90°–91° C. |
| 127 | H₃CS—(pyridyl) | —H | —C₂H₅ | —OC₂H₅ | S | 361.38 | MP. 52°–54° C. |
| 128 | H₃CS—(pyridyl) | —CH₃ | —C₂H₅ | —OC₂H₅ | S | 375.41 | MP. 67°–68° C. |
| 129 | Br—(pyridyl) | —H | —C₂H₅ | —OC₂H₅ | S | 394.19 | MP. 108°–110° C. |
| 130 | Cl—(pyridyl) | —H | —CH₃ | —OCH₃ | S | 321.68 | MP. 90°–93° C. |
| 131 | Br—(pyridyl) | —CH₃ | —CH₃ | —OCH₃ | S | 380.17 | MP 87°–88° C. |
| 132 | Cl—(pyridyl) | —CH₃ | —C₂H₅ | —OC₂H₅ | S | 328.31 | MP. 54°–55.5° C. |

TABLE I-continued $$\begin{array}{c} R-N-\!-\!-\!-N \\ R^1\diagdown\phantom{-}\diagup\phantom{O}\phantom{-}\phantom{-}\overset{Y}{\underset{\|}{\phantom{X}}}\diagup\!OR^2 \\ \phantom{R^1}\diagdown\phantom{-}\diagup O\!-\!P \\ \phantom{R^1}N\phantom{-}\phantom{-}\phantom{-}\diagdown R^3 \end{array}$$

| Compound No. | R | $R^1$ | $R^2$ | $R^3$ | Y | Molecular Weight | Physical Data |
|---|---|---|---|---|---|---|---|
| 133 | 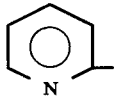 | —SOC$_2$H$_5$ | —C$_2$H$_5$ | —OC$_2$H$_5$ | S | 390.42 | MP. 25–26° C. |
| 134 | 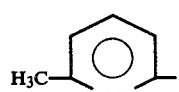 | —H | —C$_2$H$_5$ | —OC$_2$H$_5$ | S | 328.33 | MP. 46.5°–48° C. |
| 135 | 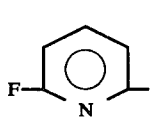 | —CH$_3$ | —CH$_3$ | —OCH$_3$ | S | 318.26 | MP. 69°–71° C. |
| 136 | 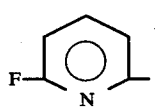 | —H | —CH$_3$ | —OCH$_3$ | S | 304.24 | MP. 74°–75° C. |
| 137 | 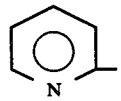 | —CH$_3$ | —C$_2$H$_5$ | —OC$_2$H$_5$ | O | 312.27 | n$_D^{25}$ = 1.5233 |
| 138 | 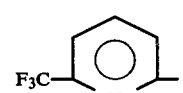 | —CH$_3$ | —CH$_3$ | —OCH$_3$ | S | 368.28 | MP. 83.5°–85.5° C. |
| 139 | 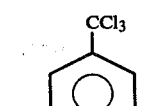 | —H | —CH$_3$ | —OCH$_3$ | S | 438.00 | MP. 94°–96° C. |
| 140 | 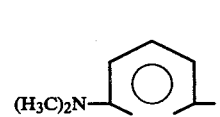 | —H | —CH$_3$ | —OCH$_3$ | S | 329.32 | MP. 83°–85° C. |
| 141 | 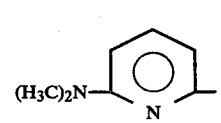 | —CH$_3$ | —CH$_3$ | —OCH$_3$ | S | 343.05 | MP. 89°–91° C. |
| 142 | 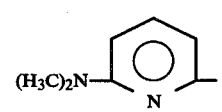 | —CH$_3$ | —C$_2$H$_5$ | —OC$_2$H$_5$ | S | 371.40 | MP. 50°–51° C. |
| 143 | 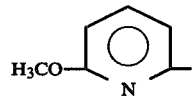 | —CH$_3$ | —CH$_3$ | —OCH$_3$ | S | 330.30 | MP. 50.5°–52° C. |

TABLE I-continued $$\begin{array}{c} R-N-N \\ R^1 \diagdown \diagup \diagdown \overset{Y}{\underset{\parallel}{P}} OR^2 \\ N-O \diagdown R^3 \end{array}$$

| Compound No. | R | $R^1$ | $R^2$ | $R^3$ | Y | Molecular Weight | Physical Data |
|---|---|---|---|---|---|---|---|
| 144 | 2-pyridyl | —CH(CH₃)₂ | —C₂H₅ | —OC₂H₅ | S | 356.39 | MP. 25°–28° C. |
| 145 | 4-Br-2-pyrimidyl | —CH₃ | —C₂H₅ | —OC₂H₅ | S | 408.22 | MP. 78°–80° C. |
| 146 | 2-pyridyl | —CH₃ | —C₂H₅ | —NHCH(CH₃)₂ | S | 341.30 | MP. 65°–67° C. |
| 147 | 2-pyridyl | —CH(CH₃)₂ | —CH₃ | —OCH₃ | S | 328.33 | MP. 45°–47° C. |
| 148 | 6-φO-2-pyridyl | —H | —CH₃ | —OCH₃ | S | 378.35 | $n_D^{25} = 1.5833$ |
| 149 | 6-φO-2-pyridyl | —CH₃ | —CH₃ | —OCH₃ | S | 392.37 | MP. 58°–60° C. |
| 150 | 2-pyridyl | —C₂H₅ | —CH₃ | —OCH₃ | S | 314.23 | MP. 43°–45° C. |
| 151 | 6-CH₃SO₂-2-pyridyl | —H | —CH₃ | —OCH₃ | S | 364.34 | MP. 113°–115° C. |
| 152 | 6-C₂H₅S-2-pyridyl | —CH₃ | —CH₃ | —OCH₃ | S | 360.40 | MP. 60°–61.5° C. |
| 153 | 5-CH₃-2-pyridyl | —CH₃ | —CH₃ | —OCH₃ | S | 314.23 | MP. 66°–68° C. |
| 154 | 6-CH₃-2-pyridyl | —H | —CH₃ | —OCH₃ | S | 300.28 | MP. 59°–61° C. |

TABLE I-continued

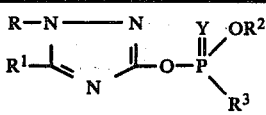

| Compound No. | R | R¹ | R² | R³ | Y | Molecular Weight | Physical Data |
|---|---|---|---|---|---|---|---|
| 155 | H₅C₂SO₂–(pyridyl) | —CH₃ | —C₂H₅ | —OC₂H₅ | S | 420.45 | MP. 69°–71° C. |
| 156 | H₅C₂SO₂–(pyridyl) | —CH₃ | —CH₃ | —OCH₃ | S | 392.39 | MP. 94°–95.5° C. |
| 157 | F–(pyridyl) | —CF₃ | —C₂H₅ | —OC₂H₅ | S | 400.29 | $n_D^{25} = 1.4932$ |
| 158 | H₃CO–(pyridyl) | —H | —CH₃ | —OCH₃ | S | 316.28 | MP. 73°–75.5° C. |
| 159 | Cl–(pyridyl) | —CH₃ | —CH₃ | —OCH₃ | S | 334.72 | MP. 84°–85° C. |
| 160 | NC–(pyridyl) | —H | —CH₃ | —OCH₃ | S | 311.18 | MP. 155°–156° C. |
| 161 | NC–(pyridyl) | —CH₃ | —CH₃ | —OCH₃ | S | 325.29 | |
| 162 | 4-H₃CO–φ-O–(pyridyl) | —CH₃ | —C₂H₅ | —OC₂H₅ | S | 450.46 | |
| 163 | 3,5-Cl₂–φ-O–(pyridyl) | —CH₃ | —C₂H₅ | —OC₂H₅ | S | 489.30 | MP. 66°–68° C. |

Preparation of Starting Materials

The substituted triazol-3-ol compounds corresponding to the formula

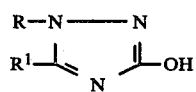

wherein R and R¹ are as hereinbefore defined and which are employed as starting materials, are novel compounds and can be prepared by a variety of procedures.

Those compounds wherein R¹ is hydrogen can be prepared by the reaction of an appropriate substituted hydrazine carboxamide with excess formic acid or triethyl orthoformate under reflux conditions with or without a solvent being present. Representative solvents include dimethyl sulfoxide, xylene and dimethylformamide. The product is thereafter recovered by cooling the reaction mixture and pouring it over ice and filtering off the solid product which precipitates. Alternatively the reaction mixture is concentrated by distillation and the solid product which precipitates is recovered by filtration. The product regardless of the method of recovery can be further purified by being either washed with a solvent and then dried or washed with water and dried. When water washing is employed it is often advantageous to neutralize the filtrate to recover any product remaining therein.

Those compounds where $R^1$ is chloro are usually prepared by chlorinating the appropriate compound wherein $R^1$ is hydrogen. This chlorinating step employs a convention chlorinating procedure wherein chlorine gas is bubbled through the triazol-3-ol compound at 10°–20° C. After the chlorination is complete, the desired product is recovered by filtration.

Those compounds wherein $R^1$ is bromo or fluoro can be prepared by conventional halogen exchange procedures wherein the appropriate triazol-3-ol compound, wherein $R^1$ is chloro, is treated with potassium bromide or cesium fluoride, respectively. The desired product is then recovered by quenching the reaction mixture with ice and filtering of the solid product.

Those compounds wherein $R^1$ is amino or alkylamino can be prepared by reacting the appropriate triazol-3-ol compound wherein $R^1$ is chloro, fluoro or bromo with ammonia or an alkyl amine in the presence of a solvent such as, for example, dimethyl sulfoxide or isopropyl alcohol and at temperatures in the range of about 45° to about 150° C. for from 1 to about 3 hours. The product can be separated by conventional techniques of quenching and filtration.

Those compounds wherein $R^1$ is alkoxy, alkylthio or phenylthio can be prepared by the reaction of an appropriate triazol-3-ol compound wherein $R^1$ is chloro, bromo, or fluoro and an appropriate alkali metal alkoxide, alkali metal alkyl- or phenylmercaptide, in the presence of an organic solvent of the type conventionally employed for such reactions.

In carrying out this reaction, the alkali metal is dissolved in an alcohol corresponding to the alkyl or phenyl group being added. The alkali metal oxy compound is inherently formed and is employed as such in the following reactions. The mercaptide is formed by adding the appropriate mercaptan to the alcohol solution. To the appropriate above mixture is added the triazol-3-ol reactant and the resulting mixture is refluxed for a time sufficient to complete the reaction, usually from about 1 to about 3 hours. The reaction products are filtered to remove any alkali metal halide, followed by solvent removal by evaporation, distillation or other conventional separatory procedures, leaving the desired product.

Those compounds wherein $R^1$ is alkylsulfinyl or sulfonyl can be prepared by reacting an appropriate triazol-3-ol with an oxidizing agent. The oxidation of any of the alkylthio substituted compounds results, at least partially, in the formation of the corresponding alkylsulfinyl substituted compound. The oxidation of one molecular of the alkylthio substituted compound to the corresponding alkylsulfinyl substituted compound or the oxidation of one molecule of a alkysulfinyl compound to the corresponding alkylsulfonyl compound requires one atom of oxygen for each sulfur atom oxidized. The oxidation of the alkylthio compound directly to the corresponding alkylsulfonyl compound, on the other hand, consumes two atoms of oxygen for each sulfur atom so oxidized.

In carrying out the various oxidation reactions to prepare the sulfonyl compounds of the present invention, it is preferable to employ an excess of the oxidizing agent, whereas in preparing the sulfinyl compounds, it is preferable not to provide oxygen appreciably in excess of the stoichiometric quantities consumed in the conversion and to employ milder reaction conditions and/or oxidants.

In many instances, the alkylsulfinyl compounds can be prepared and subjected to continuing oxidative conditions so as to be further oxidized in situ to the corresponding sulfonyl compound. In some instances, depending on the oxidizing agent and process conditions, the oxidation proceeds to the sulfonyl compound so rapidly that it is not practical to isolate the sulfinyl compound. Representative oxidizing agents for the production of the sulfinyl compounds include nitric acid and hydrogen peroxide and representative oxidizing agents to be employed in the preparation of the sulfonyl compounds include hydrogen peroxide, and perbenzoic acid.

Hydrogen peroxide, and conveniently an aqueous solution thereof, can be employed as the oxidizing agent in the production of the sulfinyl and sulfonyl containing derivatives of the present invention. In such embodiment, the reaction is carried out in the presence of a liquid reaction medium, such as trifluoroacetic acid, glacial acetic acid or a mixture of acetic acid and acetic anhydride. In a preferred procedure, the acid-anhydride mixture is employed as the liquid reaction medium. The reaction takes place at temperatures of from about 75° to about 120°C. In a convenient method, the reaction is carried out at the boiling temperature of the reaction mixture and under reflux. In carrying out the reaction, the reactants are contracted in any order or fashion, and preferably in amounts stoichiometric for the preparation of the desired product. The reaction mixture is then maintained at a temperature within the reaction temperature range until the desired degree of conversion is achieved. Following the reaction period, the sulfinyl or sulfonyl product can be separated by conventional procedures such as evaportion of the reaction medium to obtain the product as a solid residue. In an alternative procedure, the reaction mixture is washed with cold water and is thereafter filtered, centrifuged or the like to obtain the crystalline product.

Nitric acid is conveniently employed to oxidize the alkylthio starting material to the corresponding sulfinyl derivative. The reaction can be carried out in the presence of a halacarbon reaction medium such as carbon tetrachloride, methylene dichloride, ethylene dibromide, etc. In a preferred procedure, excess nitric acid is employed as the reaction medium. The reaction proceeds at temperatures between about 15° and about 120° C. Preferably, the reaction is carried out under reflux conditions at temperatures of form 80° to 120° C. and requires only a short period of time for completion, i.e., about 2 to about 7 minutes. Conveniently, the reactants are mixed and the temperature is allowed to rise to the desired temperature and maintained at or about this temperature during the refluxing.

The contacting of the reagents and separation and isolation of the desired product are all as previously described.

In an additional procedure, chlorine water can also be employed as the oxidizing agent in the preparation of alkylsulfinyl or sulfonyl derivatives from the corresponding alkylthio derivatives. When employing chlorine water as an oxidizing agent, a slurry of the alkythio containing compound to be oxidized is prepared in water and the slurry agitated while chlorine gas is bubbled in. The mixture is maintained at room temperature until no starting alkylthio material is left unoxidized. If it is desired to convert the sulfinyl compound to the sulfonyl state, the temperature is raised to about 90° C. and the mixture maintained at this temperature until oxidation is complete. /This mode of oxidation is further discussed in U.S. Pat. No. 3,415,832.

Those compounds wherein $R^1$ is alkyl are prepared by the reaction of an appropriate substituted hydrazine carboxamide with an excess of an appropriate triethylorthoester under reflux conditions in the presence or absence of a solvent. Representative solvents include dimethylsulfoxide and xylene. The product is thereafter recovered as set forth hereinbefore for compounds wherein R is hydrogen. Representative ester reactants include compounds corresponding to the formula

wherein $R^4$ is methyl, ethyl or propyl. Specific compounds include triethyl orthoacetate, triethyl ortho propionate and triethyl orthobutyrate.

Those compounds wherein $R^1$ is phenyl can be prepared by the reaction of an appropriate 2-benzoyl-2-(2-pyridinyl)hydrazine carboxamide with an alkali metal hydroxide, at a temperature of from about 25° to about 75° C. for from about one minute to about one hour, followed by acidfying the the reaction product.

Those compounds wherein $R^1$ is thiocyanato can be prepared by the reaction of an appropriate triazol-3ol compound wherein $R^1$ is chloro, bromo or fluoro and an appropriate alkali metal thiocyanate under reflux conditions for a time sufficient to complete the reaction, usually from about 1 to about 3 hours. The reaction products are filtered to remove any alkali metal halide, followed by solvent removal by evaporation, distillation or other conventional separatory procedures, leaving the desired product.

Those compounds wherein $R^1$ is trichloromethyl can be prepared by the selective chlorination of the appropriate compounds wherein $R^1$ is methyl. In this procedure, chlorine gas is passed into the appropriate triazol-3-ol compound at temperatures of from about 20° to about 30° C. in the presence of a solvent such as carbon tetrachloride for a period of from 30 minutes to about 5 hours in the presence of UV light.

Those compounds wherein $R^1$ is trifluoromethyl can be prepared by halogen exchange whereby the appropriate trichloromethyl substituted compound is treated with antimony trifluoride under conventional halogen exchange conditions.

EXAMPLE VII
1-(6-Fluoro-2-pyridinyl)-1H-1,2,4-triazol-3-ol

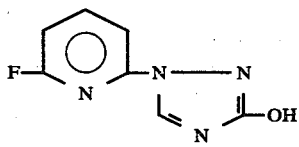

A solution was prepared by admixing 17 g (0.10 m) of 2-(6-fluoro-2-pyridinyl)hydrazinecarboxamide and 60 mls of 98 percent formic acid. This mixture was stirred and reflux for 2 hours and allowed to cool to room temperature. The insolubles were filtered off and dried to produce 3.5 g of the desired 1-(6-fluoro-2-pyridinyl)-1H-1,2,4-triazol-3-ol which melted at 290° C. with decomposition. The excess formic acid in the remaining liquid phase was distilled off under reduced pressure and the solids which precipitated were washed and dried. This product was a second crop of the desired product which also melted at 290° C. The product was recovered in a yield of 60 percent of theoretical and upon analysis, was found to have carbon, hydrogen and nitrogen contents of 46.80, 2.89 and 31.17 percent, respectively, as compared with the theoretical contents of 46.47, 2.80 and 31.10 percent, respectively, as calculated for the above named compound.

EXAMPLE VIII
1-(2-Pyridinyl)-1H-1,2,4-triazol-3-ol

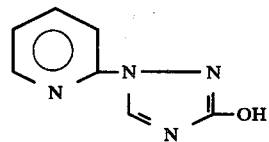

A mixture of 31.9 g (0.21 m) of 2-pyridinyl- hydrazinecarboxamide and 17.50 ml of triethylorthoformate was refluxed for 6 hours with the ethanol formed as a by-product being continuously removed by distillation thereby maintaining the reaction temperature at 130°-140° C. At the completion of the reaction, the reaction mixture was coled to 15° C. and the solid 1-(2-pyridinyl)-1H-1,2,4- -triazol-3ol product was recovered by filtration. The product after washing with methylene chloride was recovered in a yield of 25.2 g (74 percent of theoretical). The product melted at 260°-262° C. and upon analysis was found to have carbon, hydrogen and nitrogen contents of 52.26, 3.90 and 34.79 percent, respectively, as compared with the theoretical contents of 51.89, 3.73 and 34.55 percent, respectively, calculated for the above named compound.

EXAMPLE IX
1-(6-Fluoro-2-pyridinyl)-5-methyl-1H-1,2,4-triazol-3-ol

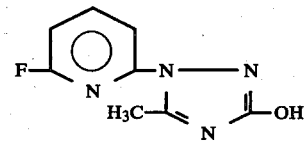

A solution was prepared by admixing 17.02 g (0.10 m) of 2-(6-fluoro-2-pyridinyl)hydrazinecarboxamide with 100 ml of triethylorthoacetate. The mixture was refluxed overnight and the reaction mixture cooled to room temperature and poured over ice water. The solids which precipitated out were recovered by filtration. The solids were washed with methylene chloride and dried under vacuum to yield 11.4 g (58.7 percent of theoretical) of the desired 1-(6-fluoro-2-pyridinyl)-5-methyl-1H-1,2,4-triazol-3-ol. The product melted at 272°-274° C. and upon analysis was found to have carbon, hydrogen and nitrogen contents of 49.58, 3.83 and 28.88 percent, respectively, as compared with the theoretical contents of 49.48, 3.63 and 28.85 percent, respectively, as calculated for the above named compound.

EXAMPLE X 1-(2-Pyridinyl)-5-methyl-1H-1,2,4-triazol-3-ol

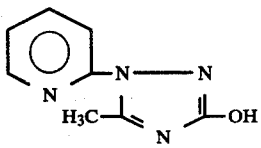

A reaction mixture was prepared by suspending 457.6 g (3 m) of 2-pyridinyl-hydrazine carboxamide in 2600 ml of triethylorthoacetate and the mixture refluxed for about 9 hours. The ethanol by-product formed was continuously removed by distillation allowing the reaction temperature to stay at 125°–130° C. The 1-(2-pyridinyl)-5-methyl-1H-1,2,4-triazol-3-ol product was recovered by filtration in a yield of 116 g (66 percent of theoretical) and was washed with chloroform. The product melted at 194°–195° C. and upon analysis was found to have carbon hydrogen and nitrogen contents of 53.87, 4.55 and 31.95 percent, respectively, as compared with the theoretical contents of 54.53, 4.57 and 31.80 percent, respectively, calculated for the above named compound.

EXAMPLE XI 1-(2-Pyridinyl)-5-(phenylthio)-1H-1,2,4-triazol-3-ol

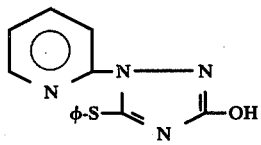

To a solution of 2.3 g (0.10 m) of sodium metal dissolved in 125 ml of methanol was added a solution of 5.51 g (0.05 m) of thiophenol in 25 ml of methanol. To this mixture was added 9.8 g (0.05 m) of 1-(2-pyridinyl)-5-chloro-1H-1,2,4-triazol-3-ol and the mixture stirred for three hours at room temperature. The methanol was removed by evaporation under vacuum and the residue which remained was taken up in water and the water insoluble solids were removed by filtration. The aqueous layer was acidified with concentrated hydrochloric acid. The white solid which precipitated was recovered by filtration and dried under vacuum to yield 9.5 g (~70 percent of theoretical) of the desired 1-(2-pyridinyl)-5-(phenylthio)-1H-1,2,4-triazol-3-ol product. The product melted at 235°–237° C. and upon analysis was found to have carbon, hydrogen and nitrogen contents of 55.87, 3.79 and 19.90 percent, respectively, as compared with the theoretical contents of 55.91, 3.93 and 20.06 percent, respectively, calculated for the above named compound.

EXAMPLE XII

5-Phenyl-1-(2-pyridinyl)-1H-1,2,4-triazol-3-ol

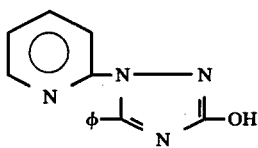

A mixture was prepared by admixing 1.84 g (0.00718 m) of 2-benzoyl-2-(2-pyridinyl)hydrazinecarboxamide with 30 ml of 10 percent sodium hydroxide. The mixture was warmed to 50° C. to dissolve the carboxamide. The solution was held at 50° C. for 10 minutes and the reaction mixture was cooled to room temperature. The reaction product was acidified with 30 ml or 50 percent acetic acid and the white solid which precipitated was recovered by filtration, washed with water and air dried. The 5-phenyl-1-(2-pyridinyl)-1H-1,2,4-triazol-3-ol product was recovered in a yield of 1.12 g (66 percent of theoretical). The product melted at 240°–241° C. and upon analysis was found to have carbon, hydrogen and nitrogen contents of 64.83, 4.35 and 22.46 percent, respectively, as compared with the theoretical contents of 65.53, 4.23 and 23.52.

EXAMPLE XIII 1-(2-Pyridinyl)-5-amino-1H-1,2,4-triazol-3-ol

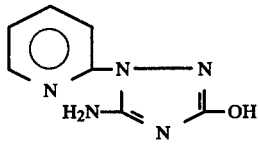

Anhydrous ammonia was bubbled into a solution containing 9.8 g (0.05 m) of 1-(2-pyridinyl)-5-chloro-1H-1,2,4-triazol-3-ol for one hour while the mixture was being heated at 140°–150° C. The reaction mixture was cooled and poured over ice water and the solid which precipitated was recovered by filtration. The recovered solid was dissolved in basic water and then acidified water concentrated hydrochloric acid. After recovery by filtration, the solids were dried under vacuum to yield 6.76 g (76.3 percent of theoretical) of the desired 1-(2-pyridinyl)-5-amino-1H-1,2,4-triazol-3-ol product (as the HCl salt). The product melted at 270°–273° C. and upon analysis was found to have carbon, hydrogen and nitrogen contents of 41.12, 4.42 and 33.25 percent, respectively, as compared with the theoretical contents of 39.35, 3.74 and 32.78 percent, respectively, calculated for the above named compound.

EXAMPLE XIV 1-(2-Pyridinyl)-5-chloro-1H-1,2,4-triazol-3-ol

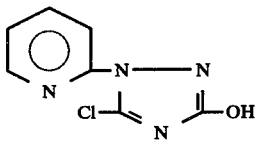

A one liter flask equipped with a dry ice condenser, gas inlet tube, thermometer and a magnetic stirrer was charged with 32.43 (0.20 m) of 1-(2-pyridinyl)-1H-1,2,4-triazol-3-ol and 300 ml of water. To this mixture was bubbled 16.3 g (0.23 m) of condensed chlorine gas at 10°–20° C. Thereafter, the reaction mixture was stirred at room temperature for one hour. The solid which formed was removed by filtration, washed with cold hexane and dried under vacuum to yield 33.7 g (85.7 percent of theoretical) of the desired 1-(2-pyridinyl)-5-chloro-1H-1,2,4-triazol-3-ol. The product melted at 146°–147.5° C. and upon analysis was found to have carbon, hydrogen and nitrogen contents of 42.69, 2.64 and 28.80 percent, respectively, as compared with the theoretical contents of 42.77, 2.56 and 28.50 percent, respectively, calculated for the above named compound.

By following the preparative procedures outlined hereinabove, the following compounds of Table II are prepared.

TABLE II

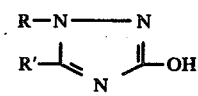

| R | R¹ | Melting Point °C. |
|---|----|-------------------|
| quinolin-2-yl | —H | 303° w/dec. |
| 3-chloropyridin-2-yl | —H | 205–207° |
| 5-chloro-4-methylpyrimidin-2-yl | —H | <340° |
| 6-(methylthio)pyridin-2-yl | —CH₃ | 255°–258° |
| 3-chloro-6-methylpyridin-2-yl | —H | <350° |
| 6-(methylthio)pyridin-2-yl | —H | 240°–242° |
| 6-chloroquinolin-2-yl | —H | 260° w/dec. |
| quinolin-2-yl | —H | 245°–247° |
| 5-(3,5-dichlorophenoxy)pyridin-2-yl | —H | 280°–282° |
| 5-(3,5-dichlorophenoxy)pyridin-2-yl | —CH₃ | 272°–273° |
| 5-chloropyridin-2-yl | —N(CH₂—CH=CH₂)₂ | |
| pyridin-2-yl | —CH₃ | 228°–230° |
| 4-methylpyridin-2-yl | —H | |
| 5-bromopyridin-2-yl | —H | 235° w/dec. |
| 5-(trifluoromethyl)pyridin-2-yl | —CH₃ | 279°–283° w/dec. |
| 5-bromopyridin-2-yl | —CH₃ | |
| 5-phenoxypyridin-2-yl | —CH₃ | 259.5°–261° |
| 5-phenoxypyridin-2-yl | —H | 203°–205° |

TABLE II-continued

R—N——N
R'⎤   ⎡
    N—OH

| R | R¹ | Melting Point °C. |
|---|----|-------------------|
| 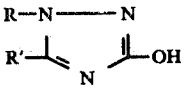 5-Cl-pyridyl | —H | 280° w/dec. |
|  3,5-diCl-4-methyl-pyridyl | —N(C₄H₉)₂ | |
| 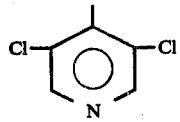 3,5-diCl-pyridyl | —H | 210°–220° w/dec. |
| 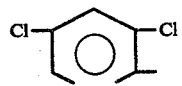 2,5-diCl-pyridyl | —H | |
| 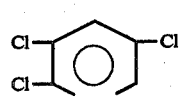 2,3,5-triCl-4-methyl-pyridyl | —Cl | |
| 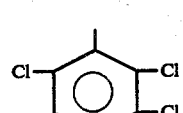 6-CF₃-pyridyl | —H | 270°–272° w/dec. |
| 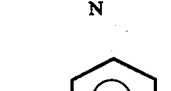 3,5-diCl-2-F-pyridyl | —H | |
| 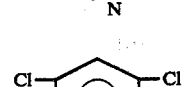 3,5-diCl-2-F-pyridyl | —CF₃ | |
| 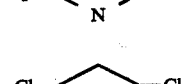 pyridyl | —H | 260° w/dec. |
| 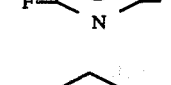 pyrazinyl | —OCH₃ | |
| 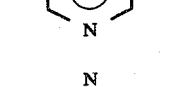 pyrazinyl | -φ | |

TABLE II-continued

R—N——N
R'⎤   ⎡
    N—OH

| R | R¹ | Melting Point °C. |
|---|----|-------------------|
| 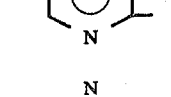 3-NO₂-pyridyl | —H | 190° w/dec. |
| 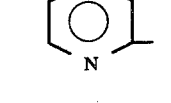 5-NO₂-pyridyl | —H | 192°–194° |
| 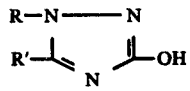 6-CF₃-pyridyl | —C₃H₅ | |
|  6-CF₃-pyridyl | —CF₃ | |
| 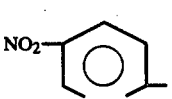 2,6-diCl-4-F-pyridyl | —Br | |
| 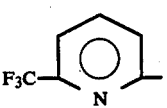 2,6-diCH₃-4-methyl-pyridyl | —C₄H₉ | |
| 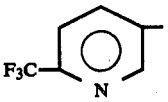 6-SO₂CH₃-pyridyl | —F | |
| 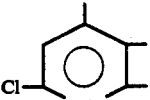 2-CN-4-Cl-pyridyl | —CCl₃ | |
| 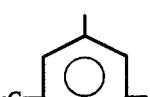 quinoxalinyl | —SO₂CH₃ | |
|  phthalazinyl | —C₃H₅ | |

TABLE II-continued

R—N—N
R'—C(=N)—OH (structure)

| R | R¹ | Melting Point °C. |
|---|---|---|
| 4-CCl₃-6-Cl-pyridin-2-yl | —H | 245°–249° |
| 5-CN-pyridin-2-yl | —H | 294°–295° |
| 4-CN-pyridin-2-yl | —CH₃ | |
| 6-(H₃CS)-pyridin-2-yl | —H | 240°–242° |
| 6-(H₃CS)-pyridin-2-yl | —CH₃ | 226°–229° |
| 6-F-pyridin-2-yl | —H | 290° w/dec. |
| 3-Cl-pyridin-2-yl | —H | 270° w/dec. |
| 3-SCH₃-pyridin-2-yl | —H | |
| 3,5-diCl-pyridin-2-yl | —H | 143°–145° |
| 5-CN-pyridin-2-yl | —CH₃ | 322°–325° |
| 5-(H₃CS)-6-CH₃-pyridin-2-yl | —H | 214°–216° |

TABLE II-continued

R—N—N
R'—C(=N)—OH (structure)

| R | R¹ | Melting Point °C. |
|---|---|---|
| 4-CH₃-3-(H₃CS)-pyridin-2-yl | —H | 225° w/dec. |
| pyridin-3-yl | —NH₂ | |
| 5-(H₃CO)-pyridin-2-yl | —H | 248° w/dec. |
| 4-CH₃-6-Cl-pyridin-2-yl | —H | 220° w/dec. |
| 4-CH₃-3,5,6-triCl-pyridin-2-yl | —H | |
| 3,4,5-triF-pyridin-2-yl | —F | |
| 4-CH₃-3,5-di(CH₃)-pyridin-2-yl | —H | |
| 4-CH₃-3,5-di(CH₃)-pyridin-2-yl | —H | |
| 6-Cl-pyridazin-3-yl | —H | 217° w/dec. |
| 5-Cl-pyrazin-2-yl | —H | 237°–238° |
| 5-Cl-pyrazin-2-yl | —CH₃ | 293°–296° w/dec. |

TABLE II-continued $$R-N-N$$
$$R'\overset{\|}{\underset{N}{C}}\overset{\|}{C}-OH$$

| R | R¹ | Melting Point °C. |
|---|---|---|
| 2,3-dichloropyrazine | —H | |
| pyridin-2-yl | —SC₂H₅ | 192°–194° |
| 5-(4-methoxycarbonylphenoxy)pyridin-2-yl | —CH₃ | 220°–222° |
| pyridin-2-yl | —SCN | 220° w/dec. |
| 5-chloropyridin-2-yl | —CH₃ | 290°–292° |
| 6-chloropyridin-2-yl | —CH₃ | 305°–306° |
| 6-fluoropyridin-2-yl | —C₂H₅ | 218°–224° |
| pyridin-2-yl | —N(CH₃)₂ | 188°–189° |
| pyridin-2-yl | —C₂H₅ | 228°–230° |
| pyridin-2-yl | —OCH₃ | 154°–155° |
| 5-chloropyridin-2-yl | —H | 305°–309° C. |
| 5-bromopyridin-2-yl | —H | 204°–205° |
| 5-bromopyridin-2-yl | —CH₃ | |
| 5-cyanopyridin-2-yl | —C₂H₅ | |
| pyridin-2-yl | —SO₂C₂H₅ | |
| pyridin-2-yl | —SC₄H₉ | |
| pyridin-2-yl | —SOC₂H₅ | 172°–174° |
| 6-phenoxypyridin-2-yl | —N(CH₃)₂ | |
| pyridin-4-yl | —SCH₃ | |
| pyridin-4-yl | —SOCH₃ | |
| pyridin-2-yl | —SCN | 215°–220° |
| pyridin-2-yl | —SO₂C₄H₉ | |

TABLE II-continued

R—N———N
R'—⧸⧹  ⧸⧹—OH
    N

| R | R¹ | Melting Point °C. |
|---|---|---|
| H₃CO—[pyridine] | —CH₃ | 255°–258° |
| H₃CO—[pyridine] | —H | 232°–235° |
| H₃C—S(O)(O)—[pyridine] | —H | 281°–284° w/dec. |
| H₅C₂—S(O)(O)—[pyridine] | —CH₃ | 269°–272° |
| (H₃C)₂N—[pyridine] | —CH₃ | 238°–241° |
| H₃C—[pyridine] | —CH₃ | 245°–248° |
| H₃C—[pyridine] | —H | 240°–242° |
| [pyridine] | —CH(CH₃)₂ | 207°–208° |

The substituted hydrazine carboxamide corresponding to the formula $$R-NHNH\overset{O}{\overset{\|}{C}}NH_2$$

wherein R is as hereinabove defined can be prepared by the reaction of an appropriate substituted hydrazino compound of the formula

R—NHNH₂ in the presence of a solvent and/or water and a mineral acid with an alkali metal cyanate.

In carrying out this reaction, the appropriate hydrazino compound in the solvent and/or water is mixed with concentrated mineral acid and the mixture stirred at a temperature of from about 20° to about 40° C. until a clear solution is formed. The alkali metal cyanate is added as an aqueous solution and the mixture stirred at room temperature until the reaction is complete, usually from about 1 to about 4 hours. The product is thereafter recovered by cooling the reaction mixture and filtering off the solid product which precipitates. The product can be further purified, if desired, by washing with a solvent such as methylene chloride and/or water and drying.

The substituted hydrazinoheterocyclic compounds corresponding to the formula $X_n$—heterocyclic—NHNH₂ wherein X and n are as hereinabove defined and heterocyclic is the same as R defined hereinabove and the two terms are employed interchangably, can be prepared by a variety of procedures.

In one method, the compounds can be prepared by the reaction of an appropriately substituted haloheterocyclic compound with hydrazine or its hydrate. This reaction can be characterized as follows:

$$X_n-R-q + NH_2NH_2 \xrightarrow{\Delta} X_n-R-NHNH_2$$

wherein X, R and n are as hereinbefore defined, q is chloro, fluoro or bromo and no attempt is made to present a balanced equation.

This procedure is especially preferred when preparing compounds wherein the hydrazino group is in a ring position ortho or para to the heterocyclic nitrogen.

In carrying out this reaction, one molar equivalent of the appropriate halo heterocyclic reactant, and a hydrogen halide acceptor, are mixed with a slight excess of the hydrazine with or without a solvent such as, for example, ethanol or isopropanol. Representative hydrogen halide acceptors include, triethylamine, pyridine, or other such conventional material. Conventionally, a large excess of hydrazine can be employed which then acts as a reactant and as the hydrogen halide acceptor.

The mixture is maintained under reflux conditions for from about 1 to about 8 hours. At the completion of the reaction, about two-thirds of the solvent is distilled off and the remaining mixture cooled, diluted with water, extracted with a solvent such as methylene chloride and the extracts dried. The insolubles are filtered off and the solvent removed by evaporation under reduced pressure leaving the desired product.

In an alternative procedure, the above reactants can be placed into a sealed reaction vessel and stirred for from about 2 to 16 hours or more at a temperature of from about 100° to about 150° C., or more, depending upon the reactants. The reaction mixture is cooled and the solid product which precipitates are recovered by filtration and washed with water and methylene chloride, filtered off and dried.

In another alternative procedure especially where the hydrazino group is in a ring position para to the heterocyclic nitrogen, an appropriately substituted 4-alkyl sulfonyl substituted compound is reacted with the hydrazine as in the above procedures. This reaction is characterized as follows:

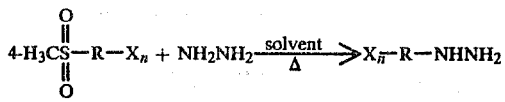

wherein R, X and n are as hereinbefore defined and no attempt has been made to present a balanced equation.

In carrying out this reaction, a mixture of the appropriately substituted 4-alkylsulfonyl compound and one of the above listed solvents are stirred while the hydrazine and a hydrogen halide acceptor (or excess hydrazine) are added dropwise. After completion of the addition, the mixture is refluxed for from about 1 to about 8 hours and then allowed to cool to room temperature. The mixture is diluted with water and the solid product recovered by filtration and then water washed and dried.

In another procedure, especially where the hydrazino group is in a ring position meta to the heterocyclic nitrogen, an appropriately substituted meta-amino heterocyclic compound is reacted with an alkali metal nitrate in the presence of a mineral acid followed the reaction of this product mixture with stannous chloride in hydrochloric acid. This reaction can be characterized as follows:

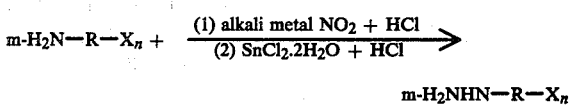

wherein R, X and n are as hereinabove defined and no attempt has been made to present a balanced equation.

In carrying out this reaction, one molar equivalent of the appropriately substituted meta-amino compound is mixed with concentrated hydrochloric acid and cooled to about 0° to −10° C. while a slight (∼10 to 20%) excess of the alkali metal nitrate reactant in water is added at a rate to maintain the reaction temperature at below about 0° C. This mixture is thereafter slowly added to a fresh solution of stannous chloride in concentrated hydrochloric acid at a rate to maintain the reaction temperature below about 0° C. The mixture is stirred for from about 1 to about 3 hours and the solution made basic. The mixture is extracted with a solvent such as methylene chloride and the extract dried filtered and distilled to recover the crude product. The crude product is purified by dissolving in dilute hydrochloric acid and extracting with methylene chloride. The aqueous phase is made basic and the desired product which precipitates is recovered by filtration, water washed and dried.

EXAMPLE XV 2-(6-Fluoro-2-pyridinyl)hydrazinecarboxamide

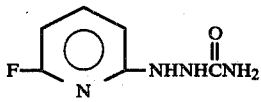

A solution was prepared by admixing 55 g (0.43 m) of 2-hydrazino-6-fluoropyridine in 240 ml of water with 40 g of concentrated hydrochloric acid in 60 ml of water. The mixture was stirred at 35° C. until a clear solution formed. To this reaction mixture was added 37 g (0.46 m) of potassium cyanate in 100 ml of water. After the addition was completed, the reaction mixture was stirred for 2½ hours at room temperature and then cooled to 10° C. on an ice bath. The 2-(6-fluoro-2-pyridinyl)hydrazinecarboxamide product was isolated by filtration and washed with methylene chloride in quantitative yield. The product melted at 210°–212° C. and upon analysis, was found to have carbon, hydrogen and nitrogen contents of 42.42, 4.23 and 32.83 percent, respectively, as compared with the theoretical contents of 42.35, 4.14 and 32.93 percent, respectively, as calculated for the above named compound.

EXAMPLE XVI 2-(2,3,5-Trichloro-4-pyridinyl)hydrazinecarboxamide

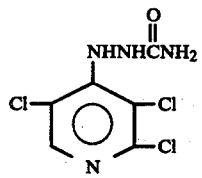

A solution was prepared by admixing 43 g (0.20 m) of 2-hydrazino-2,3,5-trichloropyridine in 100 ml of dimethylformamide with 20 g of concentrated hydrochloric acid in 250 ml of water. The mixture was stirred at 35° C. until a clear solution formed. To this reaction mixture was added 17 g (0.20 m) of potassium cyanate in 80 ml of water. After the addition was completed, the reaction mixture was stirred for 3 hours at room temperature and then cooled to 10° C. on an ice bath. The 2-(2,3,5-trichloro-4-pyridinyl)hydrazinecarboxamide product was isolated by filtration, washed with methylene chloride and recovered in a yield of 47 grams (78 percent of theoretical). The product melted at 207°–209° C.

EXAMPLE XVII

2-Benzoyl-2-(2-pyridinyl)hydrazinecarboxamide

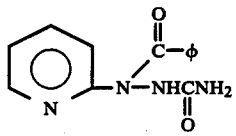

A mixture was prepared by admixing 15.22 g (0.1 mole) of 2-(2-pyridinyl)hydrazinecarboxamide with a solution of 16.2 g (0.16 m) of triethylamine in 200 ml of acetonitrile. The mixture was stirred while a solution of 21.08 g (0.15 m) of benzoyl chloride in 50 ml of acetonitrile was added. After an induction period of ∼5 minutes, the mixture exothermed reaching a peak temperature of 52° C. after 10 minutes. The reaction mixture was then stirred, without heating, for 5½ hours and then heated under reflux for 2 hours. The mixture was cooled and the crude solid 2-benzoyl-2-(2-pyridinyl)hydrazinecarboxamide product was collected by filtration. The product was washed with water and air dried and recovered in a yield of 6.1 g (24 percent of theoretical). The product was recrystallized from methanol and melted at 206° C. and upon analysis, the product was found to have carbon, hydrogen and nitrogen contents of 60.53, 4.62 and 21.47 percent, respectively, as compared with the theoretical contents of 60.92, 4.72 and 21.87 percent, respectively, calculated for the above named compound.
By following the preparative procedures set forth above, the following compounds of Table III are prepared.
TABLE III
wherein R is as follows:
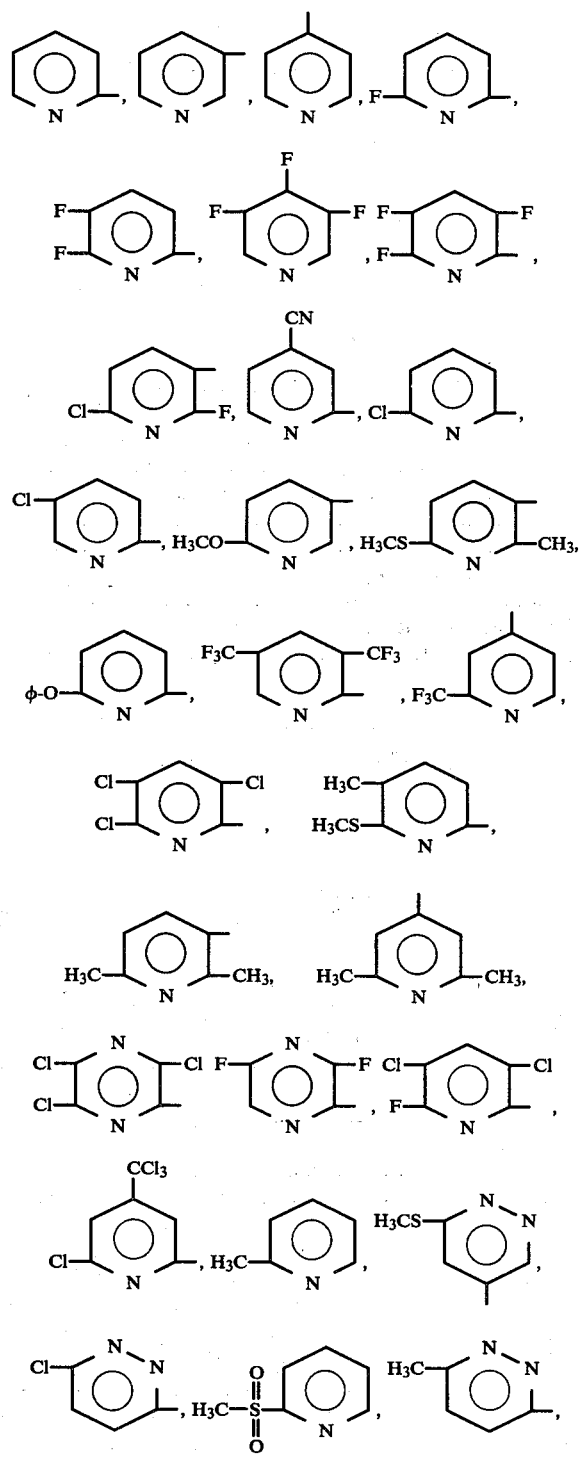
TABLE III-continued
wherein R is as follows:
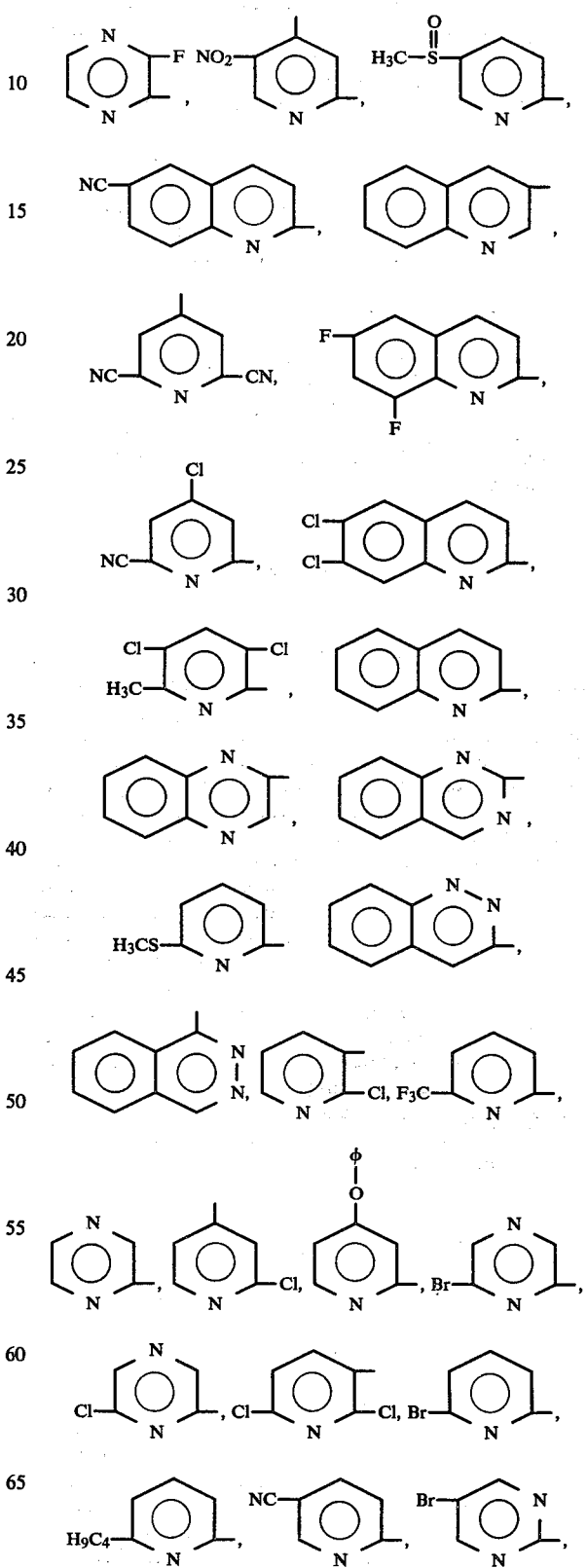

TABLE III-continued

wherein R is as follows:

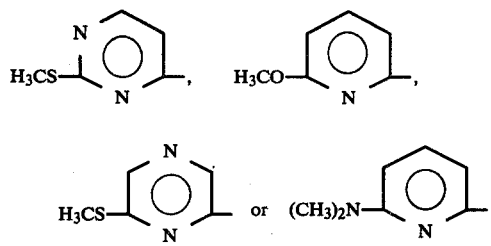

The new triazolyl phosphates of the present invention possess excellent insecticidal and acaracidal properties and are very suitable for the control of chewing and sucking insects for the protection of plants and stored goods. The compounds penetrate into the tissues of plants and/or are taken up into the plant through root uptake and are highly effective as contact and stomach poison insecticides. Owing to their low toxicity to warm-blooded animals, they are also suitable for the control of ecto and endo-parasites on and in animals.

For example, the compounds of the present invention can be employed for the control of one or more of the following arthropods, among others, and their various stages of development (larvae and eggs): insects of the families Muscidae and Culicidae, house flies (*Musca domestica*), stable flies (*Stomoxys calcitrans*) and mosquitoes (e.g. *Aedes Aegypti, Culex fatigans, Anopheles stephensi*); against insects of the families Curculonidae, Bruchidae, Dermestidae, Tenebrionidae and Chrysomelidae, e.g. granary weevils (*Sitophilus granarius*), bean beetles (*Bruchidus obtectus*), larder beetles (*Dermestes vulpinus*), mealworms (*Tenebrio molitor*), Colorado potato beetles (*Leptinotarsa decemlineata*) and their larval stages; against insects of the family Pyralididae, e.g Mediterranean flour moths (*Ephestia kuhniella*), of the faily Blattidae, cockroaches (*Blattella germanica, Periplaneta americana, Blatta orientalis*), of the family Aphididae, e.g. green peach aphids (*Myzus persicae*), of the family Pseudococcidae, e.g. citrus mealybugs (*Planococcus citri*) and of the family Locustidae, e.g. migratory locusts (*Locusta migratoria*), arachnids including the families Acaridae, Ixodidae, Tetranychidae and Argasidae.

In their use as insecticides, an insecticidal amount of the phosphorous compound per se or a composition incorporating an insecticidal amount of the compound is used as the toxicant for contact with the pest insect or its habitat. The insecticidal amount, of course, is that quantity which elicits toxic mortality among the treated pests. Generally, such insecticidal response results by contacting the target pests or their habitat with a composition containing from 0.00001 to 99 or more percent of the active compound in the total composition. Good results are achieved upon contact with a composition containing about 1000 parts of the active compound per million by weight.

Suitable compositions include those which are in the form of liquid solutions, liquid emuslifiable concentrates, and dust or granular preparations. Such can be further diluted as and where appropriate with convention diluents.

Liquid compositions containing the active compound are prepared by dissolving the active compound in a suitable inert organic solvent such as acetone, toluene, xylene, methylene chloride, chlorobenzene, ethyl ether or petroleum distillates or by dispersing the active compound in water with or without the aid of a suitable surface acting dispersing agent such as can be provided by ionic or nonionic dispersing and emulsifying agents.

The aqueous compositions may contain one or more water-immiscible solvents for the toxicants. In such compositions, the carrier comprises an aqueous emulsion, that is, a mixture of water-immiscible solvent, emulsifying agent and water. The choice of dispersing and/or emulsifying agent and the amounts thereof employed is dictated by the nature of the composition type and by the ability of the agent to facilitate the dispersion of the active toxicant compound in the aqueous carrier to produce the desired composition. Dispersing and emulsifying agents which may be employed in the compositions incude the condensation products of alkylene oxides with phenols and organic acids, alkylarylsulfonates, polyoxyethylene derivatives or sorbitan esters, complex ether alcohols, mahogany soaps, and the like. In such compositions, the surface active agents are usually employed in the amount of from 1 to 20 percent by weight of the combined weight of the surface active agent and the active compound.

In the preparation of dust compositions, the active compound is dispersed in and on a finely divided inert solid such as talcum, chalk, gypsum, and the like. In such operations, the carriers are mechanically ground with the compounds or wet with a volatile organic solvent solution thereof. Similarly, dust compositions containing the compound may be prepared from bentonite, fuller's earth, attapulgite, and other clays. Depending upon the proportions of ingredients, these dust compositions may be employed as concentrates and subsequently diluted with additional solid surface acting dispersing agent or with talc, chalk, or gypsum and the like to obtain a desired amount of active agent in a composition adapted to be applied for insect control. Also, such concentrate dust compositions may be dispersed in water with or without the aid of a dispersing agent to form spray mixtures.

Granular formulations are conveniently prepared by impregnations, such as through simple mechanical mixing, of the active compound in a presized carrier, usually of the type hereinbefore set forth.

In practice, the active compound is distributed so as to provide contact of the target insect with toxic amounts of the active compound. Such contact can be achieved through direct contact of the active compound with the target insect of by more indirect means such as by application to its food and/or habitat. Thus, for example, the active compound hereof or a composition thereof can be spread throughout the environs of the target host so as to provide direct and indirect contact thereof or bait compositions incorporating a toxic amount of the active compound or composition thereof can be readily prepared and strategically located so as to provide ultimate contact of the host species therewith.

The following examples serve to further typify the nature of the present invention and are given solely for the purpose of illustration.

EXAMPLE XVIII 25 parts by weight of one of compounds 9, 12, 16, 17, 18, 19, 20, 22, 23, 24, 25, or 29, 60 parts of fuller's earth, 10 parts of diatomaceous earth, 3 parts of an alkyl aryl sulfonate (Naccanol NR) and 2 parts of a polymerized sodium salt of a substituted benzoid alkyl sulfonic acid (Daxad No. 27) are mechanically mixed and ground together to prepare a concentrate composition in the form of a wettable powder.

Similarly, 25 parts by weight of one of compounds 30, 31, 32, 33, 34, 36, 37, 38 or 39, 65 parts xylene and 10 parts of a dimeric alkylated aryl polyether alcohol (Triton X-155), are mechanically mixed together to prepare a liquid emulsifiable concentrate composition.

In a like manner, 6 parts by weight of one of compounds 40, 41, 42, 43, 50, 51, 52, 53, 54, 55, 56, 57, 58, 59, 60, 61, 62, 64, 66, 67, or 68, 2 parts of Naccanol NR, 2 parts of Daxad No. 27, and 200 parts of water are ball-milled together to prepare a concentrate composition in the form of a water-dispersible liquid.

EXAMPLE XIX

1 Part of one of the compounds numbered 8, 11, 14, 16, 37, 42 or 44 is mixed with 99 parts of purified kerosene to obtain an oil preparation having an active ingredient concentration of 1 percent. In application, the composition can be atomized or sprayed as is.

These concentrate compositions may be further diluted in their concentrate state and/or dispersed in water to prepare aqueous compositions which have desirable wetting and penetrating properties. These compositions are adapted to be employed to treat target insect life and thus distribute the active compounds to provide contact of such inert life in insecticidal concentrations.

EXAMPLE XX

Paper cylindrical cartons about 3⅜ inches in diameter by 3¼ inches high were fitted with wire screen on the top and bottom. Into each cage were placed 6 German cockroaches (*Blattella germanica*). An aqueous dispersion prepared by admixing one of the hereinafter set forth compounds, which had been dissolved in a suitable inert solvent, with a predetermined amount of water and a surfactant, was sprayed on the cockroaches through the screen from a distance of about 15 inches using a fine spray nozzle. At the same time, additional cockroaches were sprayed with a solvent-water-surfactant mixture containing no active toxicant to serve as controls. After spraying, the cockroaches were kept for 2 days. At the end of this period, the cages were examined to determine the minimum concentration in parts of active compound per million parts of the ultimate composition (ppm) necessary to give at least a 100 percent ($LC_{100}$) kill and control of the cockroaches. The results of this examination are set forth below in Table IV.

TABLE IV

| Compound Number of Active Compound | Minimum Concentration of Active Compound in ppm to give $LC_{100}$ for German Cockroaches |
|---|---|
| 1 | 100 |
| 2 | 100 |
| 3 | 400 |
| 5 | 400 |
| 6 | ≦400 |
| 7 | 100 |
| 8 | 100 |
| 9 | 100 |
| 10 | 100 |
| 12 | 400 |
| 15 | 100 |
| 20 | 400 |
| 26 | 400 |
| 28 | 400 |
| 35 | 400 |
| 44 | 400 |
| 47 | 400 |
| 54 | 400 |
| 55 | ≦400 |
| 63 | 100 |
| 65 | 100 |
| 69 | 100 |
| 71 | 400 |
| 72 | 100 |
| 73 | ≦400 |
| Control | — |

EXAMPLE XXI

An aqueous dispersion was prepared by dispersing a predetermined amount of one of the test compounds, which had been dissolved in a suitable inert solvent, and a predetermined amount of a surfactant in a predetermined amount of water. At the same time, a water-surfactant-solvent mixture contained none of the compounds was also prepared to serve as a control. Sheets containing egg masses of codling moths were pinned to apples and the egg sheets and apples were drenched with an aqueous dispersion of one of the hereinafter set forth compounds. Separate egg masses and apples were also treated with the control mixture. The egg masses/apples were incubated under conditions conducive to the hatching of the eggs and the growth of the larvae therefrom. Ten days after treatment, the apples were examined for the presence of egg hatch and larvae. Counts of the number of larval penetration in the treated fruit were compared to the number present in the untreated control to determine the percent control obtained with the test compounds.

This examination determined the minimum concentration in parts of the active compound per million parts of the ultimate dispersion necessary to give at least a 70 percent kill and control of codling moth larvae and/or eggs and the results of this examination are set forth below in Table V.

TABLE V

| Number of active Compound | Minimum Concentration in ppm of active compound in aqueous dispersion to give $LC_{70}$ for codling moth larvae |
|---|---|
| 1 | <25 |
| 2 | <25 |
| 3 | <400 |
| 5 | 400 |
| 6 | 25 |
| 7 | 25 |
| 9 | 25 |
| 10 | 25 |
| 12 | 25 |
| 13 | 400 |
| 15 | 100 |

TABLE V-continued

| Number of active Compound | Minimum Concentration in ppm of active compound in aqueous dispersion to give LC$_{70}$ for codling moth larvae |
|---|---|
| 20 | 400 |
| 21 | 400 |
| 26 | 400 |
| 27 | 400 |
| 28 | 100 |
| 35 | <400 |
| 44 | 100 |
| 45 | 25 |
| 46 | 25 |
| 47 | <25 |
| 54 | <400 |
| 55 | 400 |
| 62 | 100 |
| 63 | <25 |
| 65 | 100 |
| 69 | 25 |
| 71 | <400 |
| 72 | 100 |
| 73 | <400 |
| 75 | <100 |
| 83 | <25 |
| 84 | 400 |
| 85 | 400 |
| 137 | >400 |
| Control | — |

EXAMPLE XXII

Seventy-five grams of air-dried soil were placed in an 8-ounce container. To the soil was added sufficient volume of a 400 ppm aqueous dispersion, prepared by admixing a predetermined amount of one of the hereinafter set forth compounds, dissolved in a suitable inert solvent, with a predetermined amount of water and a predetermined amount of a surfactant, to give various determined concentrations of the toxicant in the soil on a soil-chemical basis. The treated soil was air-dried and thoroughly mixed. To each treated container, and control containers treated with water and surfactant alone, was added 0.5 milliliters of an aqueous suspension of the eggs of the Western spotted cucumber beetle (WSCB) (70–80 eggs of 3–4 days old). Additional treated soil was used to cover the eggs and a corn seed was placed in the soil and covered with additional treated soil. The containers were thereafter maintained under conditions conducive to the growth of the seeds and the hatching of the eggs. Ten to twelve (10–12) days after treatment, the containers and the plants therein were examined to determine the minimum concentration in parts of active compound per million parts of the ultimate dispersion necessary to give at least a 100 percent kill and control of the larvae from the hatched eggs. The results of this examination are set forth below in Table VI.

TABLE VI

| Number of active Compound | Minimum Concentration in ppm of active compound in soil to give a LC$_{100}$ of WSCB Larvae |
|---|---|
| 1 | <1.5 |
| 3 | 6 |
| 4 | 25 |
| 5 | 25 |
| 6 | 25 |
| 7 | 6 |
| 8 | 25 |
| 9 | 1.5 |
| 10 | 6 |
| 11 | 25 |
| 12 | 6 |
| 13 | 6 |
| 15 | 6 |
| 20 | 25 |
| 21 | 25 |
| 26 | 25 |
| 27 | 25 |
| 35 | 25 |
| 44 | 25 |
| 45 | 6 |
| 46 | 25 |
| 47 | 1.5 |
| 54 | 25 |
| 55 | 25 |
| 63 | 25 |
| 69 | 6 |
| 70 | 6 |
| 71 | 1.5 |
| 72 | 6 |
| 73 | 25 |
| 74 | 6 |
| 75 | 25 |
| 78 | 25 |
| 79 | 25 |
| 84 | 25 |
| 85 | 25 |
| 137 | 25 |
| Control | — |

EXAMPLE XXIII

In this operation, aqueous dispersions were prepared by admixing one of the hereinafter set forth compounds, dissolved in a suitable inert solvent, with a predetermined quantity of water and a predetermined amount of a surfactant to give aqueous dispersions containing varying predetermined amounts of one of the compounds as the sole active toxicant. Separate cotton plant leaves were thoroughly wetted by briefly dipping into one of the dispersions and the wetted leaves placed in an open petri dish and permitted to dry. After the leaves were dry, 5 live beet armyworm larvae, approximately late 2nd instar were placed in each petri dish. In identical operations, 5 live late 2nd instar beet armyworm larvae were placed in control petri dishes, the leaf therein having been wetted with a solution containing only water and surfactant. The dishes were maintained under moist conditions conducive for the growth of the beet armyworm larvae for a period of about 5 days. At the end of the 5-day period, the dishes were examined to determine the minimum concentration in parts of the active compound per million parts of the ultimate dispersion necessary to give at least a 100 percent kill and control the beet armyworm larvae. The results of this examination are set forth below in Table VII.

TABLE VII

| Number of active Compound | Minimum Concentration in ppm of active compound in dispersion to give LC$_{100}$ for beet armyworm larvae |
|---|---|
| 1 | 25 |
| 2 | <25 |
| 3 | 400 |

TABLE VII-continued

| Number of active Compound | Minimum Concentration in ppm of active compound in dispersion to give LC$_{100}$ for beet armyworm larvae |
|---|---|
| 6 | 100 |
| 7 | 25 |
| 8 | 100 |
| 9 | 25 |
| 10 | <25 |
| 12 | 400 |
| 13 | 400 |
| 15 | 100 |
| 20 | 100 |
| 44 | 100 |
| 45 | 400 |
| 46 | 400 |
| 47 | 400 |
| 54 | 100 |
| 55 | 400 |
| 62 | 25 |
| 63 | <25 |
| 65 | 25 |
| 69 | 100 |
| 71 | 100 |
| 73 | 100 |
| 75 | 100 |
| 83 | 25 |
| 137 | 400 |
| Control | — |

EXAMPLE XXIV

In this operation, aqueous dispersions were prepared by admixing one of the hereinafter set forth compounds, dissolved in a suitable inert solvent, with a predetermined quantity of water and a predetermined amount of a surfactant to give aqueous dispersions of varying predetermined amounts of one of the compounds as the sole active toxicant. Separate 3 inch discs cut from tobacco plant leaves were thoroughly wetted by briefly dipping into one of the dispersions and the wetted leaves placed in an open petri dish and permitted to dry. After the leaves were dry, 5 live tobacco budworm larvae, approximately late 2nd instar were placed in each petri dish. In identical operations, 5 like live tobacco budworm larvae were placed in control petri dishes, the leaf therein having been wetted with a solution containing only water and surfactant. The dishes were maintained under moist conditions at about 80° F. conducive for the growth of the tobacco budworm larvae for a period of about 2 days. At the end of the 2-day period, the dishes were examined to determine the minimum concentration in parts of the active compound per million parts of the ultimate dispersion necessary to give at least a 100 percent kill and control of the tobacco budworm larvae. The results of this examination are set forth below in Table VIII.

TABLE VIII

| Number of active Compound | Minimum Concentration in ppm of active compound in dispersion to give LC$_{100}$ for tobacco budworm larvae |
|---|---|
| 1 | 400 |
| 6 | 100 |
| 7 | 400 |
| 10 | 400 |
| 15 | 400 |
| 28 | <400 |
| 47 | 400 |
| 54 | 100 |
| 62 | 400 |
| 63 | 400 |
| 75 | >400 |
| 83 | <25 |
| 137 | >400 |
| Control | — |

EXAMPLE XXV

Aqueous dispersions were prepared by admixing one of the hereinafter set forth compounds, dissolved in a suitable inert solvent with a predetermined quantity of water and a predetermined amount of a surfactant to give aqueous dispersions containing varying predetermined amounts of one of the compounds as the sole toxicant. Separate chili pepper plants were infested with 20 green peach aphids and the plants sprayed with one of the dispersions to run off. In a like manner, 20 green peach aphids were place on control plants and the plants sprayed to run off with a solution containing only water and surfactant. The plants were maintained under conditions conducive to the growth of the plants and aphids. After a period of two days, the plants were examined to determine the minimum concentration in parts of the active compound per million parts of the ultimate dispersion necessary to give at least 90 percent kill and control of the green peach aphids. The results of this examination are set forth below in Table IX.

TABLE IX

| Number of active Compound | Minimum Concentration in ppm of active compound in dispersion to give LC$_{90}$ for green peach aphid |
|---|---|
| 2 | >25 |
| 6 | 25 |
| 10 | >25 |
| 35 | 100 |
| 46 | 25 |
| 47 | >400 |
| 54 | 400 |
| 55 | 400 |
| 62 | 100 |
| 63 | 25 |
| 72 | 400 |
| 75 | 25 |
| 83 | >25 |
| 137 | 25 |
| Control | — |

EXAMPLE XXVI

Aqueous dispersions were prepared by admixing one of the hereinafter set forth compounds, dissolved in a suitable inert solvent, with a predetermined quantity of water and a predetermined amount of a surfactant to give aqueous dispersions containing varying predetermined amounts of one of the compounds as the sole toxicant. Separate cotton plants were infested with 20 two spotted spider mites and the plants sprayed with one of the dispersions to run off. In a like manner, 20 two spotted spider mites were placed on control plants and the plants sprayed to run off with a solution containing only water and surfactant. The plants were maintained under conditions conducive to the growth of the plants and mites. After a period of two days, the plants were examined to determine the minimum concentration in parts of the active compound per million parts of the ultimate dispersion necessary to give at least 95 percent kill and control of the two spotted spider mites. The results of this examination are set forth below in Table X.

TABLE X

| Number of active Compound | Minimum Concentration in ppm of active compound in dispersion to give LC$_{95}$ for two spotted spider mite | |
|---|---|---|
| 2 | 400 | |
| 6 | 400 | |
| 7 | 400 | |
| 10 | 100 | |
| 44 | 400 | |
| 46 | 400 | |
| 47 | <400 | |
| 55 | 100 | |
| 62 | 400 | |
| 63 | 400 | |
| 69 | 400 | (90 percent control) |
| 72 | 400 | |
| 75 | >400 | |
| 83 | 100 | |
| 137 | 100 | |
| Control | — | |

What is claimed is:
1. A compound corresponding to the formula

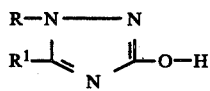

wherein R represents a nitrogen containing heterocyclic radical corresponding to the formulae

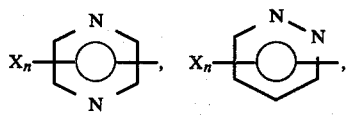

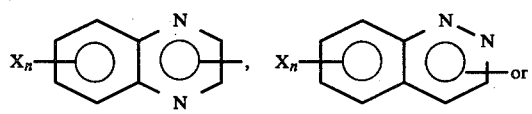

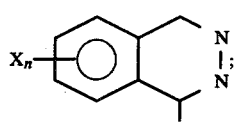

each X independently represents chloro, fluoro, bromo, nitro, alkyl of 1 to 4 carbon atoms, amino, mono- or dialkylamino wherein each alkyl group independently contains from 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, cyano, trifluoromethyl, trichloromethyl, phenoxy or substituted phenoxy of the formula

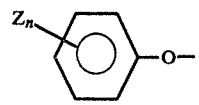

wherein each Z independently represents chloro, fluoro, bromo, nitro, cyano, alkoxy of 1 to 4 carbon atoms or alkylthio of 1 to 4 carbon atoms, with the proviso that when either n is 2 or 3, all X groups are sterically compatible with each other and all Z groups are sterically compatible with each other; Y represents oxygen or sulfur; each n can independently represent an integer of from 0 to 3, inclusive; R$^1$ represents hydrogen, chloro, fluoro, bromo, alkyl of 1 to 4 carbon atoms, cycloalkyl of 3 to 6 carbon atoms, phenyl, phenylthio, alkoxy of 1 to 4 carbon atoms, alkylthio of 1 to 4 carbon atoms, alkylsulfinyl of 1 to 4 carbon atoms, alkylsulfonyl of 1 to 4 carbon atoms, thiocyanato, trifluoromethyl, trichloromethyl, amino, mono- or dialkylamino wherein each alkyl group independently contains from 1 to 4 carbon atoms.

2. A compound as defined in claim 1 wherein R is a heterocyclic radical corresponding to one of the formulae

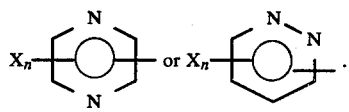

3. A compound as defined in claim 2 wherein the heterocyclic radical is

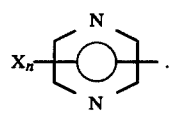

4. The compound as defined in claim 3 which is 1-(6-chloro-2-pyrazinyl)-1H-1,2,4-triazol-3-ol.
5. The compound as defined in claim 3 which is 1-(6-chloro-2-pyrazinyl)-5-methyl-1H-1,2,4-triazol-3-ol.
6. A compound as defined in claim 2 wherein the heterocyclic radical is

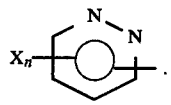

7. The compound as defined in claim 6 which is 1-(6-chloro-2-pyridazinyl)-1H-1,2,4-triazol-3-ol.

* * * * *